(12) United States Patent
Takamori et al.

(10) Patent No.: US 11,494,581 B2
(45) Date of Patent: Nov. 8, 2022

(54) OBJECT COLLATING DEVICE AND OBJECT COLLATING METHOD

(71) Applicant: FUJIFILM Toyama Chemical Co., Ltd., Tokyo (JP)

(72) Inventors: Tetsuya Takamori, Tokyo (JP); Shinji Haneda, Tokyo (JP)

(73) Assignee: FUJIFILM TOYAMA CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 17/123,385

(22) Filed: Dec. 16, 2020

(65) Prior Publication Data

US 2021/0103766 A1    Apr. 8, 2021

Related U.S. Application Data

(63) Continuation of application No. PCT/JP2019/030254, filed on Aug. 1, 2019.

(30) Foreign Application Priority Data

Aug. 31, 2018   (JP) .............................. JP2018-163363

(51) Int. Cl.
*G06T 7/30*    (2017.01)
*G06K 9/62*    (2022.01)
(Continued)

(52) U.S. Cl.
CPC .............. *G06K 9/6215* (2013.01); *A61J 1/03* (2013.01); *A61J 7/0084* (2013.01);
(Continued)

(58) Field of Classification Search
CPC ..................... G06T 7/30; G06T 7/0012; G06T 2207/30004; G16H 30/40; G06V 30/153; G06K 9/6215
See application file for complete search history.

(56) References Cited

U.S. PATENT DOCUMENTS

| 2012/0200596 A1 | 8/2012 | Gotou et al. |
| 2013/0170732 A1 | 7/2013 | Gotou et al. |

(Continued)

FOREIGN PATENT DOCUMENTS

| CN | 104173190 A | 12/2014 |
| CN | 104717952 A | 6/2015 |

(Continued)

OTHER PUBLICATIONS

International Preliminary Report on Patentability and Written Opinion of the International Searching Authorty (Forms PCT/IB/326, PCT/IB/373, and PCT/ISA/237) for International Application No. PCT/JP2019/030254, dated Mar. 11, 2021, with English translation of the Written Opinion.

(Continued)

*Primary Examiner* — Antonio A Caschera
(74) *Attorney, Agent, or Firm* — Birch, Stewart, Kolasch & Birch, LLP

(57) ABSTRACT

It is an object of the present invention to provide an object collating device and an object collating method that enable matching of images of a dividable medical article with desirable accuracy and easy confirmation of matching results. In the object collating device according to the first aspect, when the object is determined to be divided, the first image for matching is collated with the image for matching (the second matching image) for the objects in the undivided state, so that the region to be matched is not narrowed, and matching of the images of the dividable medical article is achieved with desirable accuracy. In addition, since the first and second display processing is performed on the images for display determined to contain the objects of the same type, matching results can easily be confirmed.

9 Claims, 30 Drawing Sheets

(51) Int. Cl.
*G16H 30/40* (2018.01)
*G16H 20/13* (2018.01)
*A61J 1/03* (2006.01)
*A61J 7/00* (2006.01)
*G06T 7/00* (2017.01)
*G06V 10/44* (2022.01)
*G06V 30/148* (2022.01)
*G06V 10/75* (2022.01)
*G06V 30/10* (2022.01)

(52) U.S. Cl.
CPC .............. *G06T 7/0012* (2013.01); *G06T 7/30* (2017.01); *G06V 10/443* (2022.01); *G06V 30/153* (2022.01); *G16H 20/13* (2018.01); *G16H 30/40* (2018.01); *A61J 2205/30* (2013.01); *A61J 2205/50* (2013.01); *G06T 2207/30004* (2013.01); *G06V 10/759* (2022.01); *G06V 30/10* (2022.01); *G06V 2201/05* (2022.01)

(56) References Cited

U.S. PATENT DOCUMENTS

| | | |
|---|---|---|
| 2013/0221082 A1 | 8/2013 | Botten |
| 2013/0342676 A1 | 12/2013 | Amano et al. |
| 2014/0002631 A1 | 1/2014 | Amano et al. |
| 2015/0170373 A1 | 6/2015 | Yonaha et al. |
| 2017/0264867 A1 | 9/2017 | Amano et al. |
| 2018/0174292 A1 | 6/2018 | Takamori |

FOREIGN PATENT DOCUMENTS

| | | |
|---|---|---|
| CN | 107920956 A | 4/2018 |
| EP | 2959881 A1 | 12/2015 |
| JP | 7-262378 A | 10/1995 |
| JP | 2005-122360 A | 5/2005 |
| JP | 2013-66533 A | 4/2013 |
| JP | 2013-144100 A | 7/2013 |
| JP | 2014-67342 A | 4/2014 |
| JP | 2018-27242 A | 2/2018 |
| WO | WO 2012/005004 A1 | 1/2012 |
| WO | WO 2013/021543 A1 | 2/2013 |
| WO | WO 2015/152225 A1 | 10/2015 |

OTHER PUBLICATIONS

International Search Report (Form PCT/ISA/210) for International Application No. PCT/JP2019/030254, dated Oct. 15, 2019, with English translation.

Derganc et al., "Real-time automated visual inspection of color tablets in pharmaceutical blisters," Real-Time Imaging, vol. 9, 2003, pp. 113-124.

Extended European Search Report for European Application No. 19855204.4, dated Sep. 28, 2021.

Chinese Office Action and Search Report for Chinese Application No. 201980042147.8, dated May 30, 2022, with an English translation.

FIG.8
(a) 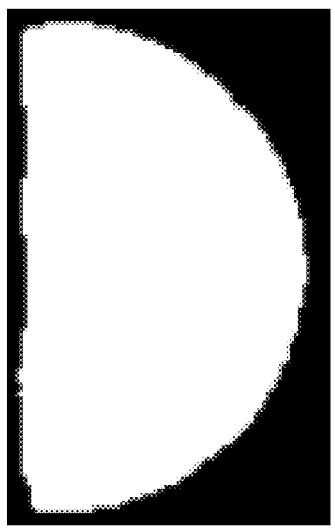 (b) 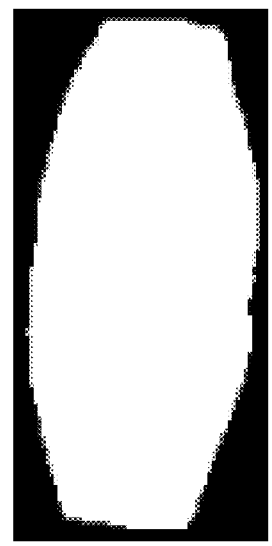

FIG.15
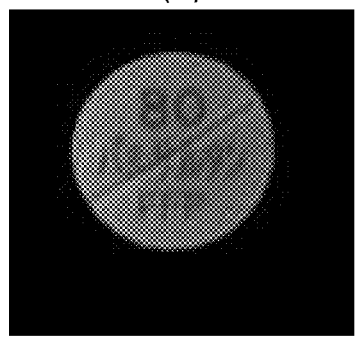
(a)
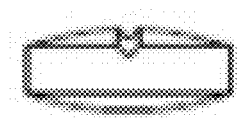
(b)
(c)
(d)

FIG.16
(a)
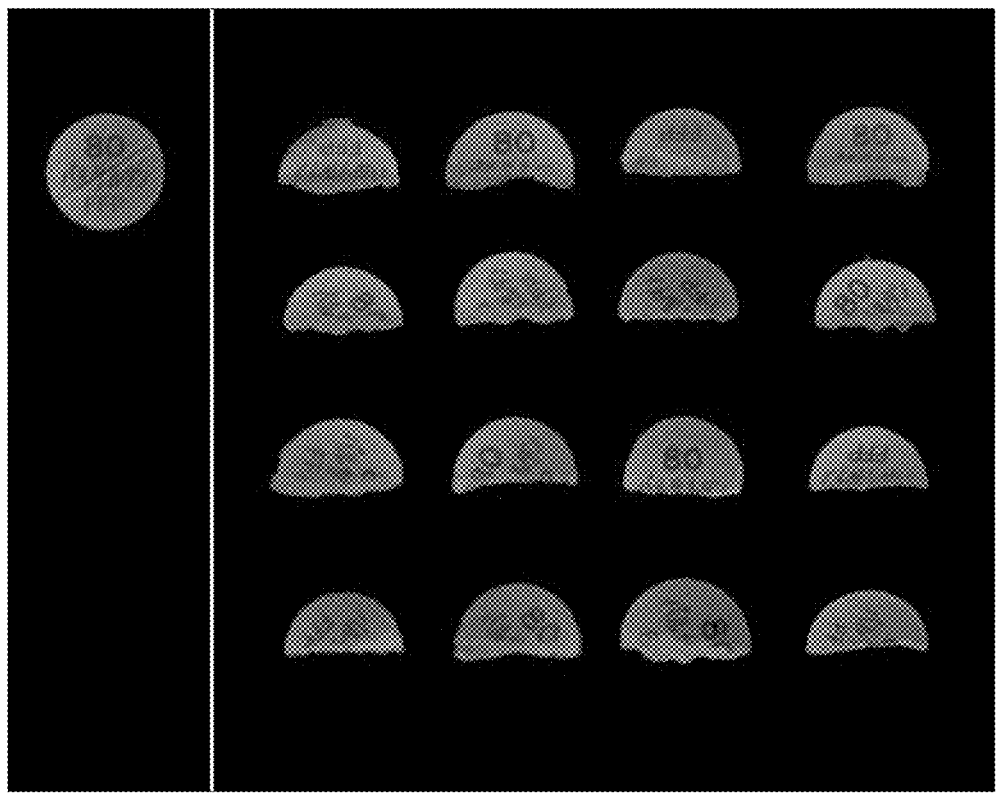
(b)
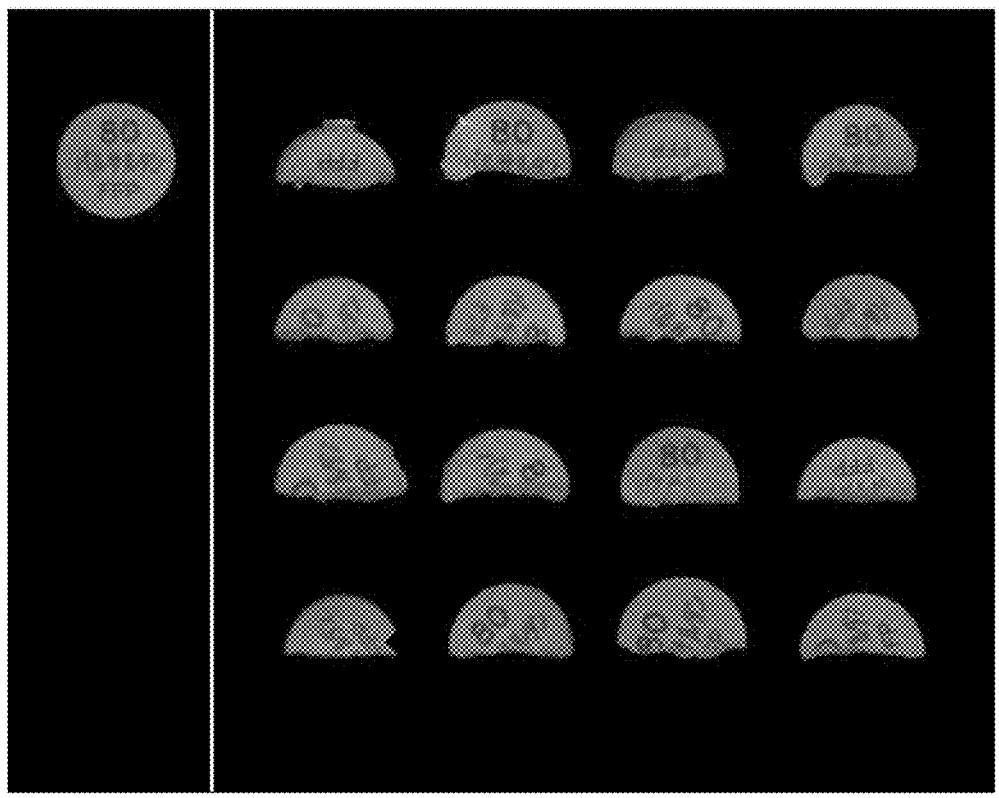

FIG.17
(a) 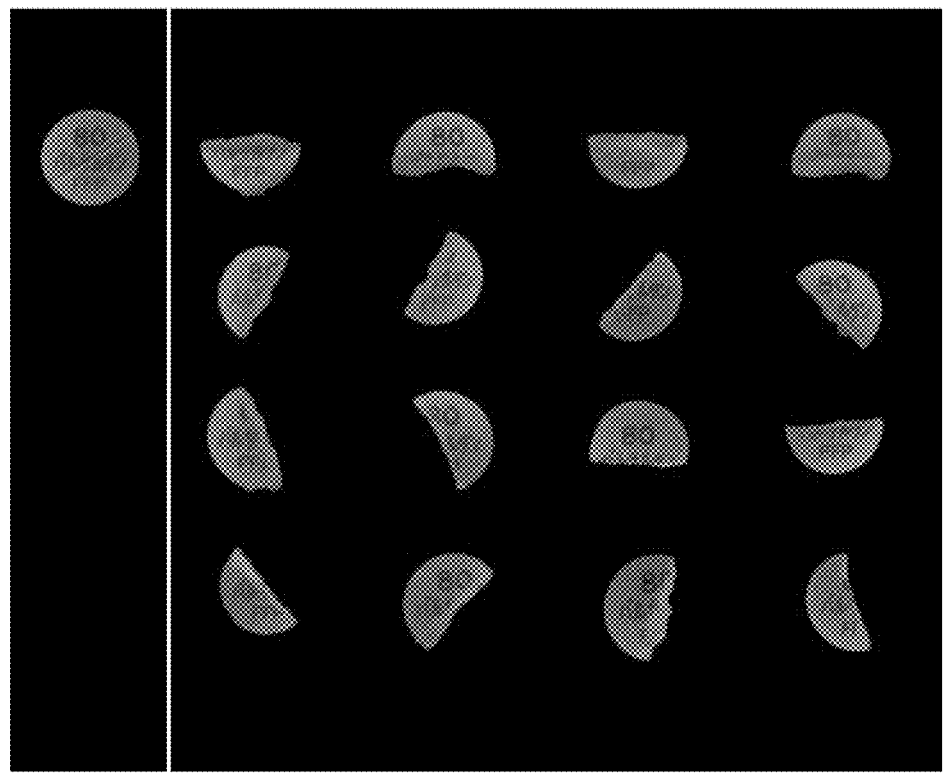
(b) 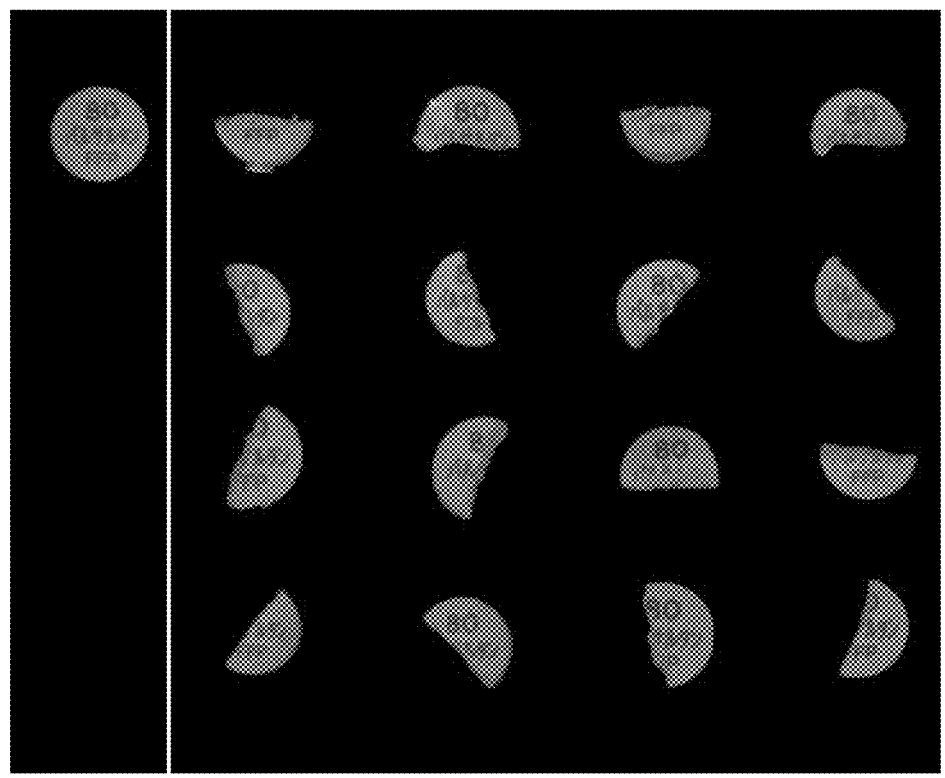

(a)
(b)

FIG.20
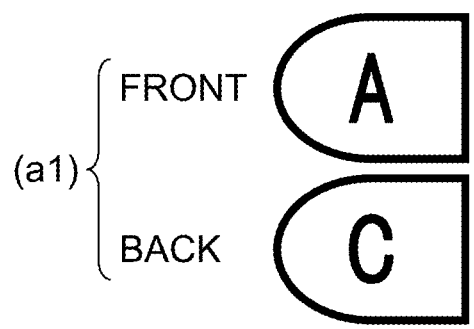
(a1) FRONT A / BACK C
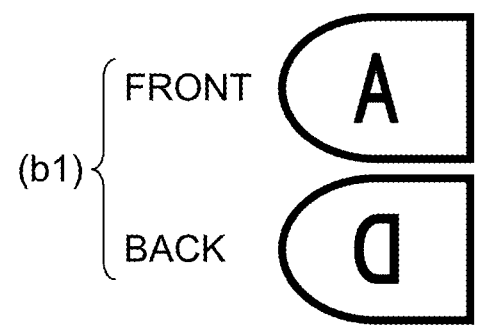
(b1) FRONT A / BACK D
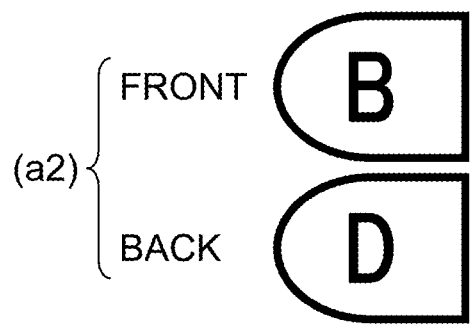
(a2) FRONT B / BACK D
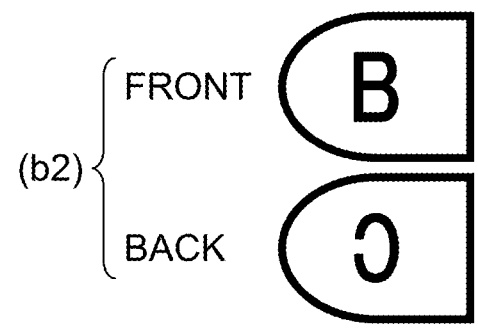
(b2) FRONT B / BACK C FIG.25
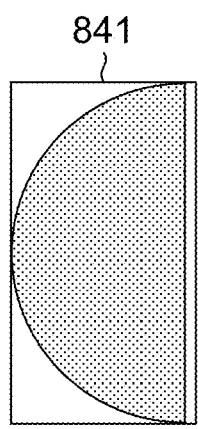
841
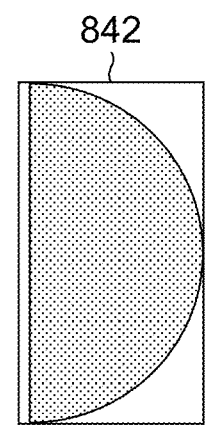
842

OBJECT COLLATING DEVICE AND OBJECT COLLATING METHOD

CROSS-REFERENCE TO RELATED APPLICATIONS

The present application is a Continuation of PCT International Application No. PCT/JP2019/030254 filed on Aug. 1, 2019 claiming priority under 35 U.S.C § 119(a) to Japanese Patent Application No. 2018-163363 filed on Aug. 31, 2018. Each of the above applications is hereby expressly incorporated by reference, in its entirety, into the present application.

BACKGROUND OF THE INVENTION

1. Field of the Invention

The present invention relates to an object collating device and an object collating method for image matching of dividable medical articles.

2. Description of the Related Art

In hospital facilities and pharmacies, audits of drugs and differentiation of medications to be brought in are performed. Since performing these tasks visually imposes a heavy workload on pharmacists and others, technology to support audits or differentiation has been developed. When performing audits or differentiation, tablets may be divided depending on the prescription and other conditions, and systems for auditing such divided tablets (variant tablets) are also known.

For example, WO2013/021543 (Patent Literature 1) describes an audit of the number of variant tablets by pattern matching the variant tablets pattern, which is a shape pattern of the variant tablets, with a medicine package band image.

CITATION LIST

Patent Literature 1: WO2013/021543

SUMMARY OF THE INVENTION

When a tablet is divided, the identification information provided on the tablet, such as printing and engraving, may be interrupted. In addition, the orientation of printing, engraving, and the like on the captured image of a tablet is irregular, making it difficult for users to see and confirm the captured image or the image used for matching if it is displayed as it is. However, in Patent Literature 1 described above, only the number of variant tablets (divided tablets) is counted, and these problems are not considered, which makes it difficult to confirm the audit results. In addition, in Patent Literature 1, variant tablet patterns are generated by dividing a standard-shaped tablet pattern (the pattern of an undivided tablet) by the number of divisions of a variant tablet, and matching is performed between the captured images of the variant tablets and the standard-shaped tablet patterns in the divided state. However, if the matching is performed by using a master image in the divided state, a region to be matched is narrowed, and thus different tablets may be erroneously determined as "the identical tablet" only by a slight match. Furthermore, in Patent Literature 1, divisions other than those for tablets are not considered.

In this manner, the technology of the related art has low matching accuracy of images of dividable medical articles, and it is difficult to confirm the matching results.

In view of such circumstances, it is an object of the present invention to provide an object collating device and an object collating method that enable matching of images of a dividable medical article with desirable accuracy and easy confirmation of matching results.

In order to achieve the object described above, an object collating device according to a first aspect of the present invention includes: a first image acquisition part configured to acquire a first image for matching based on a first captured image of an object, the object being a dividable medical article; a second image acquisition part configured to acquire a second image for matching based on a second captured image of the object in an undivided state; a division determination part configured to determine whether or not the object contained in the first captured image is divided; a collation part configured to collate the first image for matching and the second image for matching when the object is determined to be divided; and a display control part configured to cause a display device to display an image for display determined to contain an object of the same type to the first image for matching based on the result of the collation, and perform a first display processing for displaying the objects with outlines thereof aligned in orientation or a second display processing for displaying the objects with identification information attached thereto aligned in orientation.

In the first aspect, when the object is determined to be divided, the first image for matching is collated with the image for matching (the second image for matching) for the objects in the undivided state so that the region to be matched is not narrowed as in Patent Literature described above, and matching of the images of the dividable medical article is achieved with desirable accuracy. In addition, since the first and second display processing is performed on the images for display determined to contain the objects of the same type, matching results can easily be confirmed. Note that the first and second captured images can be uses as-is as the first and second images for matching, or the first and second captured images may be applied with image processing (for example, enlargement, reduction, rotation, region extraction, region emphasis). A "dividable medical article" is defined as an article that can be divided, whether or not the article itself is used (for example, there is a type of package for tablets and the like that can be divided, but the package itself is not used, and it is the tablets that are used).

In the object collating device according to a second aspect of the present invention, in the first aspect, the object collating device according to claim 1, wherein the first image acquisition part acquires the first image for matching for a front surface and a back surface of the object, the second image acquisition part acquires the second image for matching for the front surface and the back surface of the object in the undivided state, the collation part performs the collation for the front surface and the back surface of the object, and the display control part selects the first image for matching for the front surface and/or the back surface of the object and causes the display device to display the first image for matching.

In the object collating device according to a third aspect of the present invention, in the first or second aspects, the display control part aligns divided lines of the objects generated by being divided in the first display processing in orientation to align an orientation of the outlines. A straight line generated when the circular object is divided can be exemplified as the divided line, the divided line is not limited thereto. Note that in the first and second display processing, it is preferable to align the positions of the objects with respect to the divided lines (for example, align the objects so that the objects are positioned on one of the upper, lower, left, and right sides of the divided lines) in addition to aligning the orientation of the divided lines.

In the object collating device according to a fourth aspect of the present invention, in one of the first to the third aspects, the collation part performs collation based on an outline and/or identification information of the object.

In the object collating device according to a fifth aspect of the present invention, in one of the first to the fourth aspects, the collation part extracts part of a region including the object and/or the identification information in the first image for matching and performs collation on the part of the region.

In the object collating device according to a sixth aspect of the present invention, in one of the first to the fifth aspects, the division determination part determines that the object is divided when the outline of the object has a predetermined shape. For example, a determination can be made based on the distribution of pixels indicating the object in the captured image. Note that the term "predetermined shape" may include, for example, a semi-circular shape, a semi-oval shape, and a rectangle with a specified range of aspect ratio but is not limited to these examples.

In the object collating device according to a seventh aspect of the present invention, in one of the first to the sixth aspects, the collation part performs collation using images applied with processing for emphasizing identification information as the first image for matching and/or the second image for matching. According to the seventh aspect, matching is achieved with desirable accuracy.

In the object collating device according to an eighth aspect of the present invention, in one of the first to the seventh aspects, the medical article is any one of a tablet, a package containing a tablet, or a package containing a capsule-type drug. The shape of the tablet is not specifically limited. The package may be a sheet-type package configured to allow tablets or capsule-type drugs to be taken one by one.

In the object collating device according to the ninth aspect, in any one of the first to eight aspects, the identification information includes printing and/or engraving provided on the object. Printing and engraving may be done by letters, numbers, symbols, figures, and combinations thereof, and may be colored.

In order to achieve the object described above, an object collating method according to a tenth aspect of the present invention includes: a first image acquisition step for acquiring a first image for matching based on a first captured image of an object, the object being a dividable medical article; a second image acquisition step for acquiring a second image for matching based on a second captured image of the objects in the undivided state; a division determination step configured to determine whether or not the object contained in the first captured image is divided; a collating step for collating the first image for matching and the second image for matching when the object is determined to be divided; and a display control step for causing a display device to display an image for display determined to contain the object of the same type in the first image for matching based on the result of the collation, and performing a first display processing for displaying the objects with outlines thereof aligned in orientation or a second display processing for displaying the objects with identification information attached thereto aligned in orientation.

According to the tenth aspect, matching of the images of the dividable medical articles is achieved with desirable accuracy as in the first aspect. Also, the matching results can easily be confirmed.

To the object collating method of the tenth aspect, the same configuration as in the second to the ninth aspects may be further included. Also, a program for making the object collating device of these aspects or a computer execute the object collating method and a non-temporary recording medium that records computer-readable codes of the program may also be mentioned as an aspect of the present invention.

As described thus far, according to the object collating device and the object collating method of the present invention, matching of images of dividable medical articles can be matched with desirable accuracy, and matching results can easily be confirmed.

BRIEF DESCRIPTION OF THE DRAWINGS

FIG. 8 is a drawing illustrating a situation where it is determined whether or not a tablet is a divided tablet.

FIG. 15 is a drawing illustrating examples of the tablet.

FIG. 16 is a drawing illustrating examples of display by a first display processing.

FIG. 17 is a drawing illustrating examples of display by a second display processing.

FIG. 20 is still another drawing for explaining matching for an oval tablet.

FIG. 25 is a drawing illustrating examples where the circumscribed rectangle is displayed in an upright position.

DESCRIPTION OF THE PREFERRED EMBODIMENTS

With reference to the accompanying drawings, embodiments of the object collating device and the object collating method according to the present invention will be described in detail below.

First Embodiment

Figure 1:
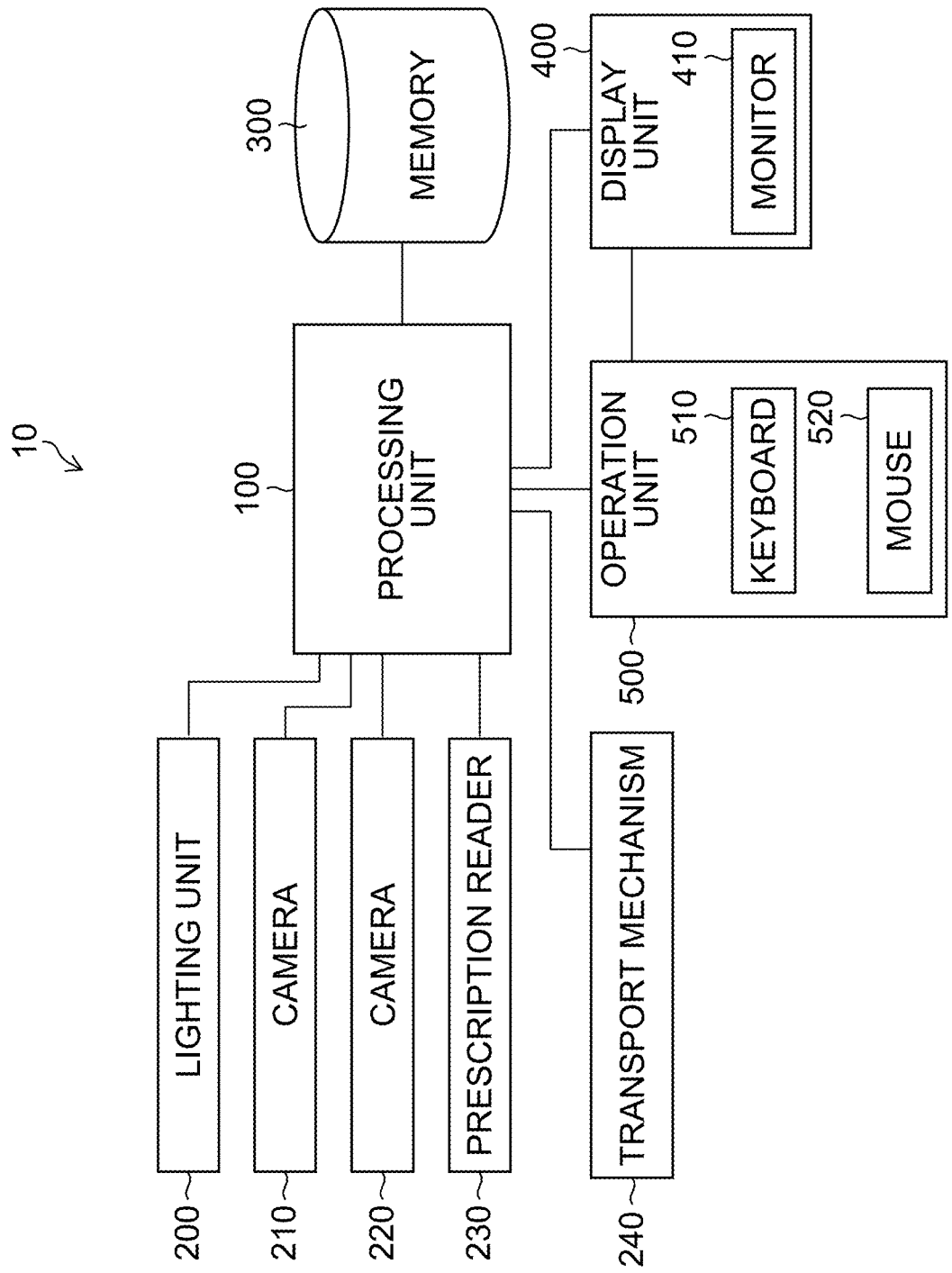
FIG. 1 is a drawing illustrating a configuration of a drug identification device according to a first embodiment.

FIG. 1 is a drawing illustrating a configuration of a tablet identification device 10 (object collating device, tablet identification device) according to a first embodiment of the present invention. The tablet identification device 10 includes a processing unit 100, a memory 300, a display unit 400, an operation unit 500, and a transport mechanism 240, and the processing unit 100 is connected to a lighting unit 200, a camera 210 (first image acquisition part), a camera 220 (first image acquisition part), and a prescription reader 230.

Figure 2:
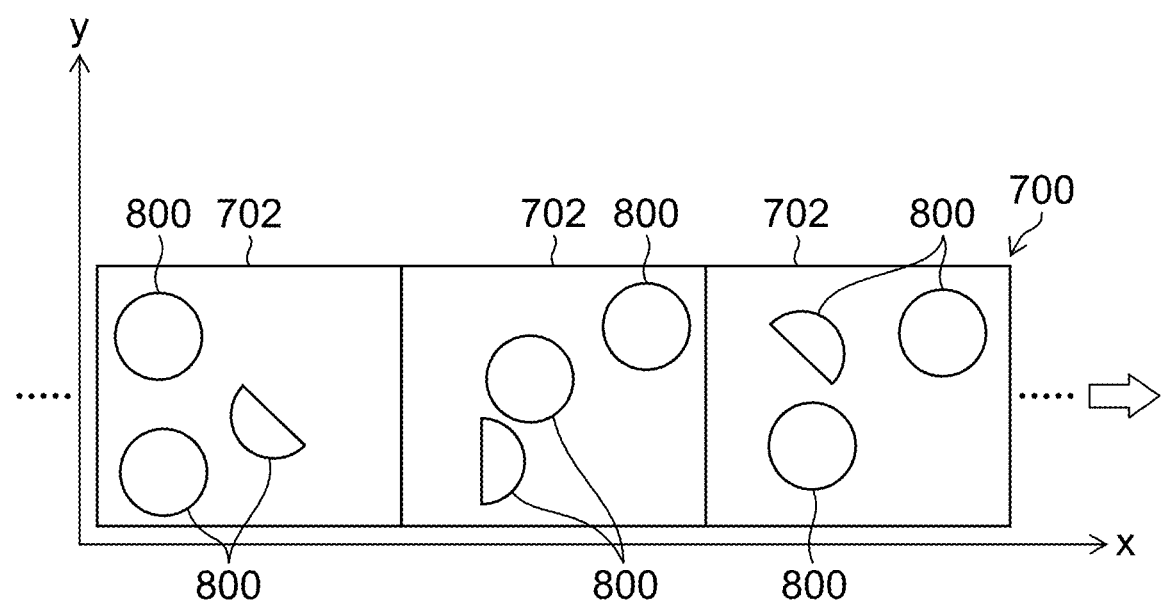
FIG. 2 is a drawing illustrating a state in which separately packaged drugs are transported.
Figure 3:
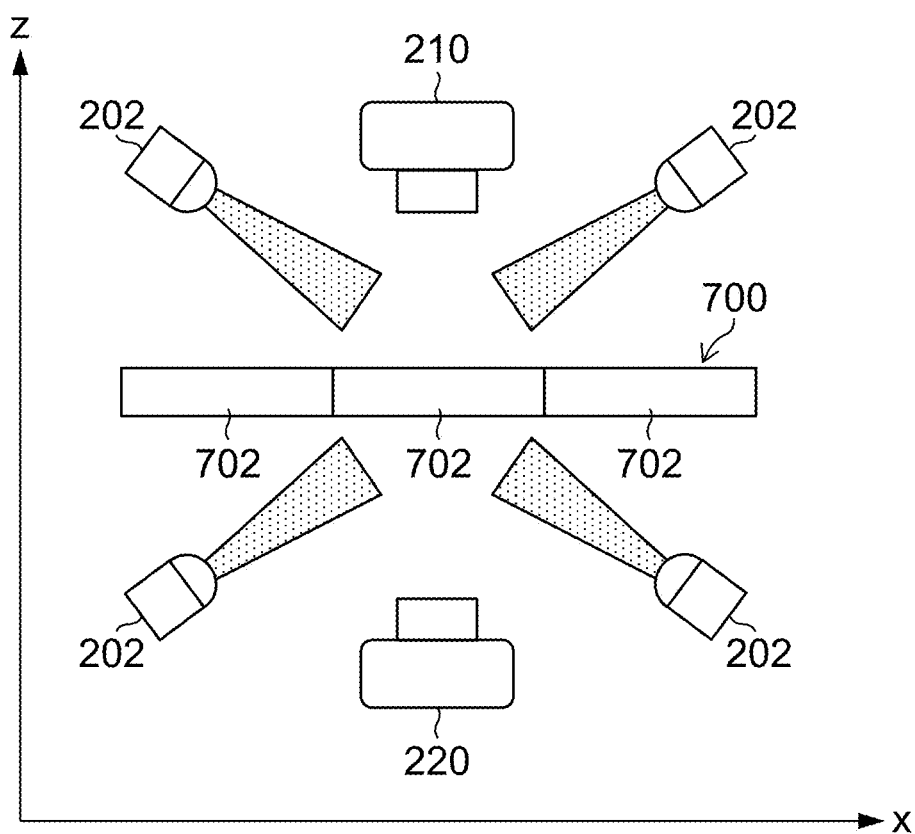
FIG. 3 is a side view illustrating the arrangement of light sources and cameras.
Figure 4:
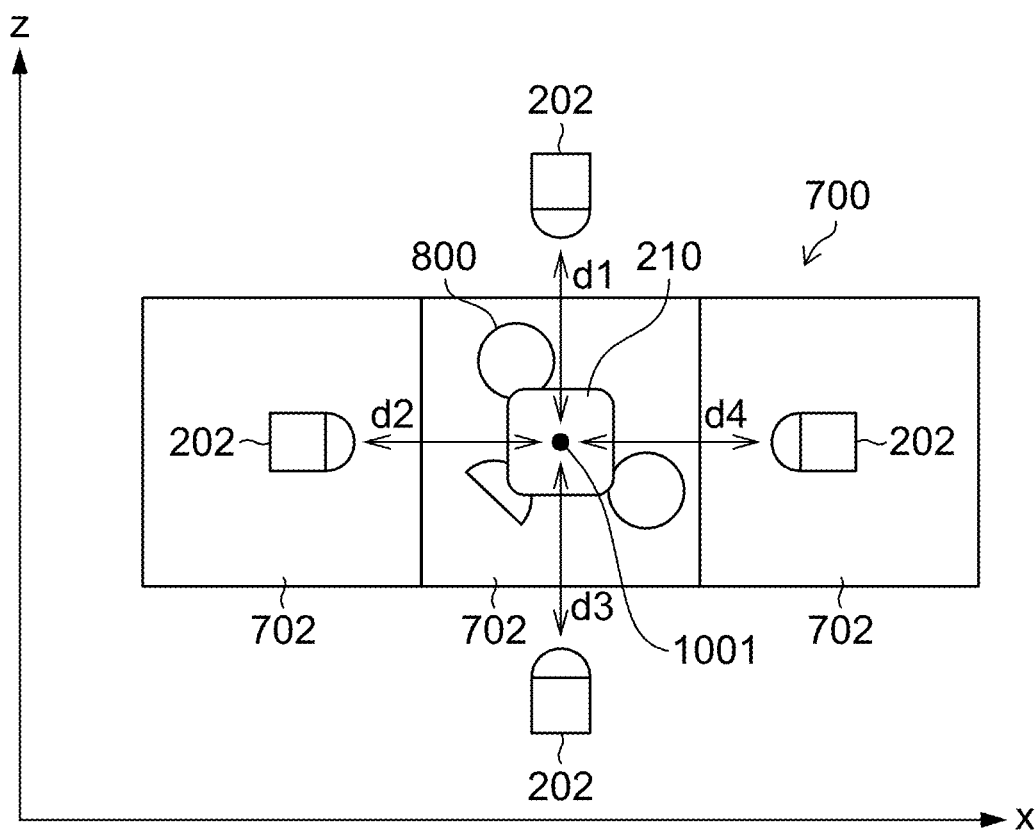
FIG. 4 is a plan view illustrating the arrangement of light sources and cameras.

The camera 210 and the camera 220 include a digital camera. As illustrated in FIG. 2, the camera 210 is disposed on the perpendicularly upper side (the +Z side of FIG. 3) of the medicine package band 700 including continuous package bags 702 (medicine package), and a camera 220 is disposed on the perpendicularly lower side (the −Z side of FIG. 3) of the medicine package band 700, and images of the tablets 800 (tablets, objects) divided in the package bag 702 are captured from the top and bottom (a plurality of different orientations) to acquire images (first captured image) of front surfaces and back surfaces. The package bags 702 (medicine package band 700) is transported by the transport mechanism 240 in the +X orientation in FIG. 2 (an axis along the longitudinal orientation of the medicine package band 700; the orientation of an arrow in FIG. 2), and a plurality of light sources 202 included in the lighting unit 200 illuminate the package bags 702 from four orientations for image capturing. In FIG. 3, the spacing (d1, d2, d3, d4) between each of the plurality of light sources 202 and the image-capturing optical axis 1001 of the cameras 210, 220 is the same. In other words, the plurality of light sources 202 and the image-capturing optical axis 1001 are equally spaced (d1=d2=d3=d4).

A prescription reader 230 reads prescription information. For example, OCR (Optical Character Recognition) is used to read information including a patient's name, a prescribed drug and its quantity, and the like from a prescription written on paper. If a barcode or other information indicating information about the prescribed drug is recorded on the prescription, the information about the prescribed drug, its quantity and other information may be read from the barcode. A user, such as a physician or a pharmacist, may read the prescription and enter the prescription information (prescription data) with an input device such as a keyboard 510 and/or a mouse 520 of the operation unit 500.

<Configuration of Processing Unit>

Figure 5:
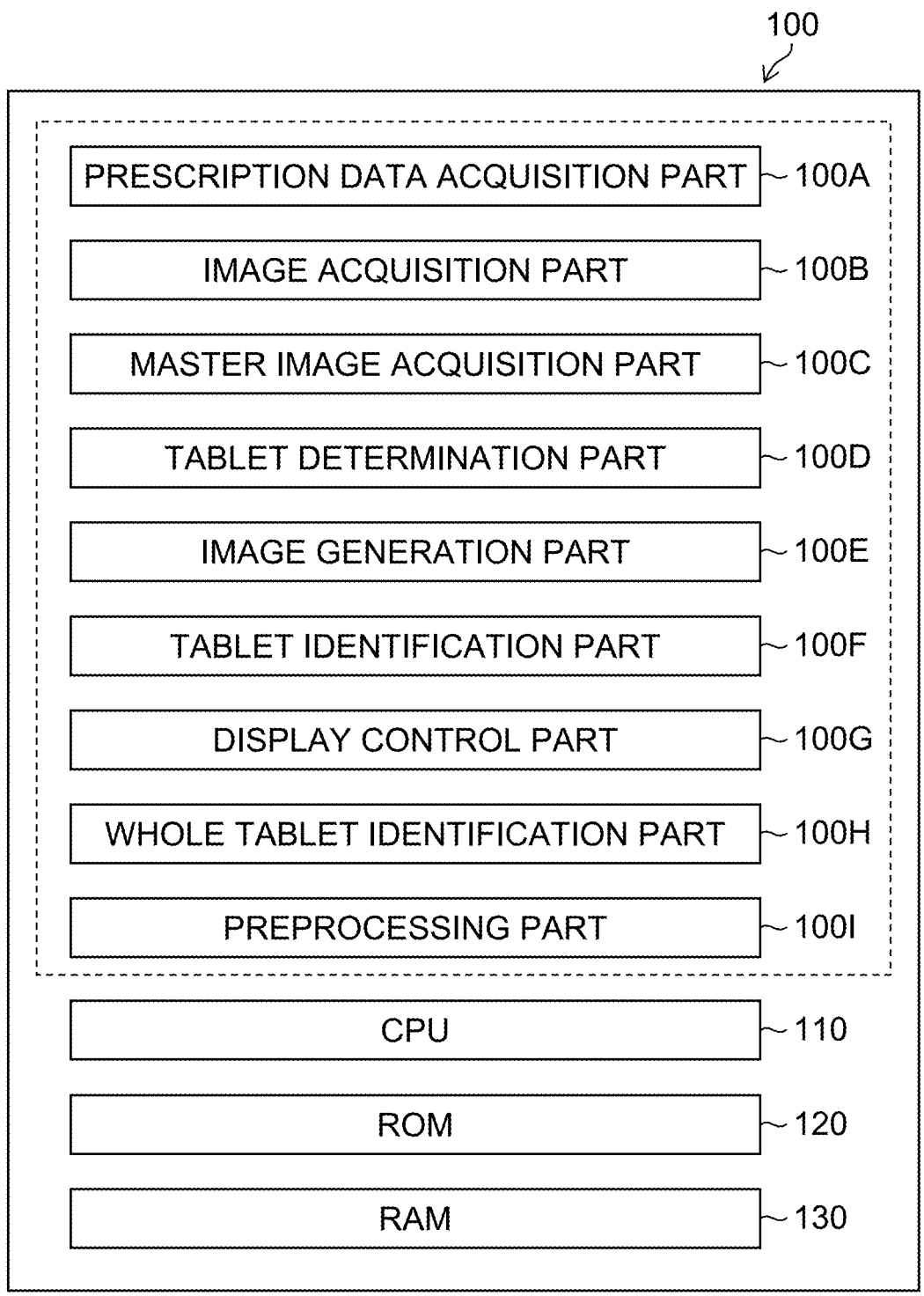
FIG. 5 is a drawing illustrating a configuration of a processing unit.

The processing unit 100 identifies the drug separately packaged in the package bags 702 based on such as the images captured by the cameras 210 and 220 and the information read by the prescription reader 230. As illustrated in FIG. 5, the processing unit 100 includes: a prescription data acquisition part 100A (prescription data acquisition part), an image acquisition part 100B (image acquisition part, first image acquisition part), a master image acquisition part 100C (master image acquisition part, second image acquisition part), a tablet determination part 100D (tablet determination part, division determination part), an image generation part 100E (image generation part), a tablet identification part 100F (tablet identification part), a display control part 100G (display control part), a whole tablet identification part 100H (whole tablet identification part), and a preprocessing part 100I (preprocessing part, collation part). The processing unit 100 includes a CPU 110 (CPU: Central Processing Unit), a ROM 120 (ROM: Read Only Memory), and a RAM 130 (RAM: Random Access Memory).

The functions of the processing unit 100 described above can be realized using various processors (processors). Various processors include, for example, a CPU (Central Processing Unit), which is a general-purpose processor that executes software (programs) to realize various functions. The various processors described above also include a Programmable Logic Device (PLD), which is a processor that can change a circuit configuration after manufacturing GPU (Graphics Processing Units) dedicated to image processing and a FPGA (Field Programmable Gate Array). In addition, a dedicated electrical circuit and the like, which is a processor having a circuit configuration specifically designed for execution of specific processing, such as an ASIC (Application Specific Integrated Circuit), is also included in the various processors described above.

The functions of each part may be realized by a single processor or by a plurality of processors of the same or different type (for example, a plurality of FPGAs, or a combination of the CPU and the FPGA, or a combination of the CPU and the GPU). Also, a plurality of functions may be achieved by a single processor. Examples in which the plurality of functions are configured with a single processor firstly include an aspect in which a combination of one or more CPUs and software constitute a single processor, and the processor realizes a plurality of functions as being represented by a computer. Secondly, as being represented by a System on Chip (SoC), an aspect of using a processor achieving functions of the entire system with a single IC (Integrated Circuit) chip is also applicable. In this manner, the various functions are configured as a hardware structure, using one or more of the various processors described above. Furthermore, the hardware structure of these various processors is, more specifically, an electrical circuit (circuitry) in which circuit elements such as semiconductor elements are combined. These electrical circuits may be an electrical circuit that uses logical sums, logical products, logical negations, exclusive logical sums, and logic operations combining these circuits to achieve the functions described above.

When the processor or the electrical circuit described above executes software (program), the processor (computer) readable code of the software to be executed is stored in a non-temporary recording medium such as a ROM 120

(ROM: Read Only Memory), and the processor refers to the software. The software to be stored on a non-temporary recording medium includes a program for executing the object collating method and the tablet identification method described below in the present invention. The code may be recorded on a non-temporary recording medium such as various magneto-optical recording devices, a semiconductor memory, and the like instead of ROM. For example, RAM 130 (RAM: Random Access Memory) is used as a temporal storage area for processing using software and, for example, data stored in an EEPROM (Electronically Erasable and Programmable Read Only Memory), not illustrated, can also be referenced. The processing performed by these processors or electrical circuits is overseen by the CPU 110.

<Configuration of Memory>

Figure 6:
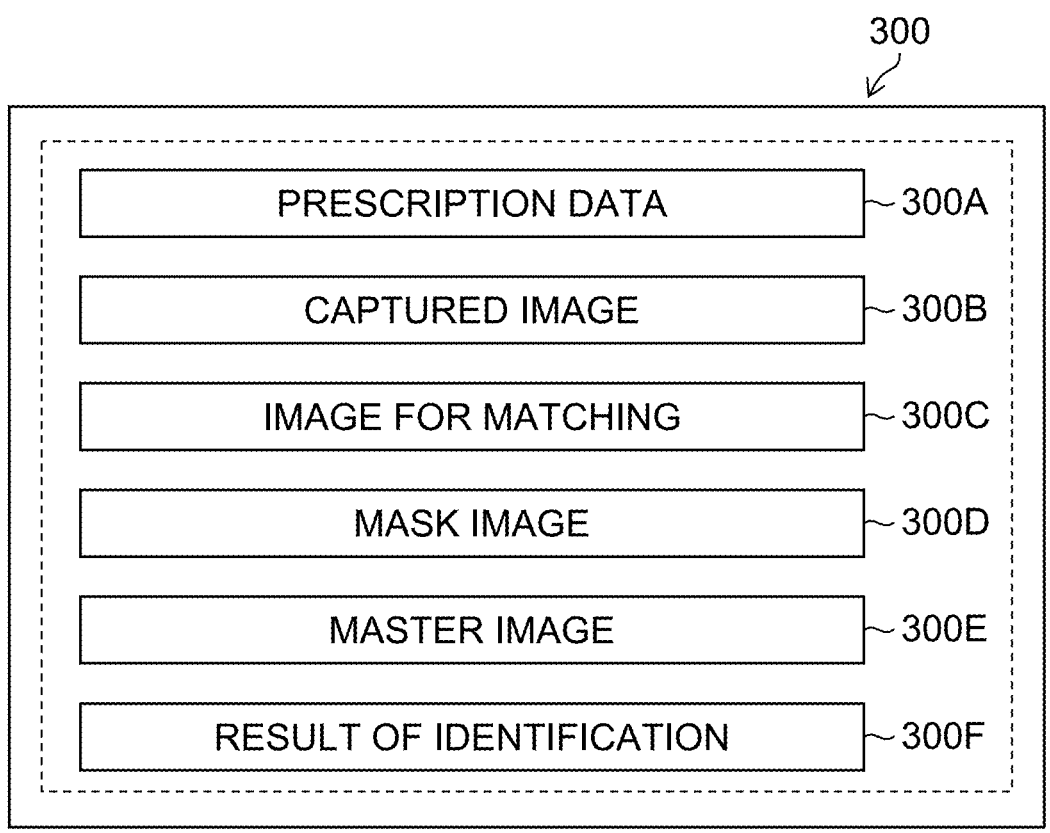
FIG. 6 is a drawing illustrating information stored in a memory.

The memory 300 includes a non-temporary recording medium such as a CD (Compact Disk), a DVD (Digital Versatile Disk), a hard disk (Hard Disk), various semiconductor memories, and other non-temporary recording media and its control unit, and the information illustrated in FIG. 6 is stored in association with each other. Prescription data 300A is prescription information read by the prescription reader 230, or information entered, edited, and the like by the user based on the prescription. The prescription data 300A may allow for entry of the name of a specific drug based on a generic name of a drug listed in the prescription, or exchange between the branded drug and the generic drug, and the like. The captured image 300B (the first captured image) is an image of the drug taken by the camera 210, 220 and includes images of the front surface and the back surface of the drug. When a plurality of drugs (tablets) are included in the captured image, an extracted image of a region for a single drug from the captured image may be used as the captured image 300B. The image for matching 300C (a first image for matching based on the first captured image) is an image containing the tablet region generated from the captured image for a tablet determined to be a divided tablet and is used for template matching with the master image. The mask image 300D includes a first mask image, which is a mask image for tablet region extraction, and a second mask image, which is a mask image for engraving and/or printing region extraction. These mask images may be binarized. The master image 300E (the second image for matching based on the second captured image) is an image including the front surface and the back surface of the tablet (object) in an undivided state and is a reference image for template matching. The result of identification 300F is the result of identifying the type and surface of the tablet indicated by the image for matching.

<Configuration of Display Unit and Operation Unit>

The display unit 400 is provided with a monitor 410 (display device) displaying input images, processing results, information stored in the memory 300, and the like. The operation unit 500 includes a keyboard 510 and a mouse 520 as input devices and/or pointing devices, and the user can perform operations required for the execution of the object collating method of the present invention or a tablet identification method, described later, such as an image capturing instruction, a tablet identification instruction, a display aspect (first display processing or second display processing) selection, and the like via these devices and the screen of the monitor 410 (described below). Note that the monitor 410 may be configured with a touch panel and may be operated via the touch panel.

<Processing of Tablet Identification Method>

Figure 7:
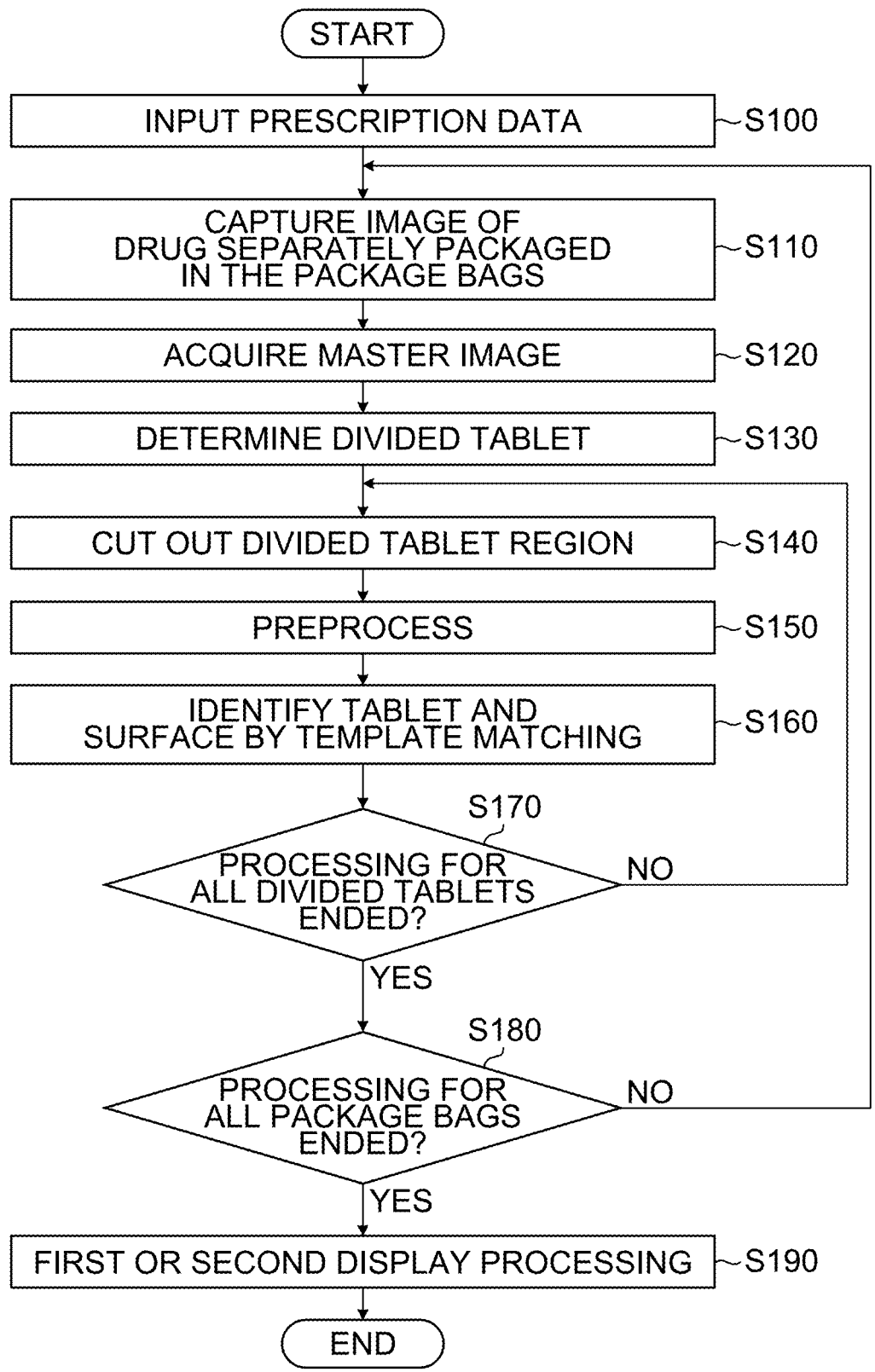
FIG. 7 is a drawing illustrating a drug identification method according to the first embodiment.

Referring to the flowchart of FIG. 7, the processing of the object collating method (tablet identification method) with the tablet identification device 10 having the configuration described above will be described.

The prescription data acquisition part 100A enters prescription information via the prescription reader 230 (Step S100: prescription data acquisition step). The entered prescription information may be acquired as prescription data as-is, or information entered, edited, or the like by the user via the operation unit 500 based on the prescription may be acquired as prescription data. The prescription data acquisition part 100A also enters characteristics of the drug (for example, type, shape, and color of the tablet, etc.) recognized by the user visually or otherwise, or information such as the drug name, quantity, dosing method, and the like described in a notebook such as the so-called "medication handbook" as relevant information in response to the user's operation, and then adds or uses such information to or instead of the prescription data.

The image acquisition part 100B controls the cameras 210, 220 to acquire a captured image (the first captured image) of the drug (tablet) separately packaged in the package bags 702 from a plurality of different directions (±Z orientation in FIGS. 2, 3; perpendicularly from the top and bottom) (step S110: image acquisition step, first image acquisition step). In this case, the package bag 702 is illuminated by the lighting units 200 and the light sources 202.

The master image acquisition part 100C acquires a master image including the front surface and the back surface of the tablet (object) in an undivided state based on the acquired prescription data (Step S120: master image acquisition step, second image acquisition step). The master image acquisition part 100C may acquire a master image 300E stored in the memory 300 or may acquire a master image from an external server, database, or the like via a communication line, not illustrated. The master image acquisition part 100C may capture an image (second captured image) of the tablet (object) in an undivided state via the camera 210, the camera 220, and the image acquisition part 100B, and apply image processing necessary to the captured image and acquire the same as a master image.

<Determination of Divided Tablet>

The tablet determination part 100D (division determination part) determines (finds out) whether or not the tablet (object) contained in the captured image (the first captured image) is a divided tablet (divided or not) (Step S130: tablet determination step, division determination step). This determination can be made, for example, by the following methods 1 and 2, and the tablet determination part 100D can determine tablets that have not been identified as a "whole tablet" and tablets that have been determined to be "unknown" by these methods to be "divided tablets". In the first embodiment, the tablet is a form of "dividable medical articles".

<Method 1: Identification Based on Captured Image and Master Image>

The whole tablet identification part 100H (division determination part) identifies the type of the undivided tablet (whole tablet) based on the captured image and the master image. Specifically, the whole tablet is identified by template matching between a captured image and a master image. The template matching can be performed by a known method (for example, a method described in Japanese Patent Application Laid-Open No. 2014-67342).

<Method 2: Determination Based on Mask Image>

The tablet determination part 100D (division determination part) can be determined based on symmetry (asymmetry) of the pixel distribution in the mask image as follows.

Figure 9:
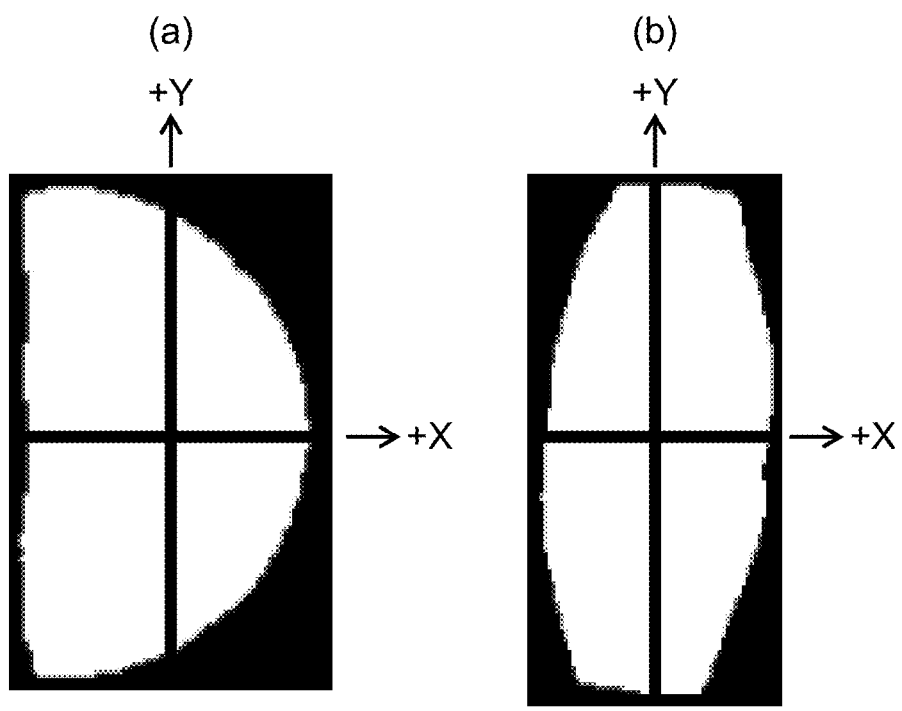
FIG. 9 is a drawing illustrating another situation where it is determined whether or not a tablet is a divided tablet.

The whole tablets are often symmetrical in both the horizontal and vertical orientations (when aligned in orientation in the horizontal direction or the vertical direction), while divided tablets are considered to be asymmetrical, as described below. FIG. 8 illustrates a binarized mask image of a tablet in a captured image generated by using a layered network constructed by machine learning (for example, a neural network for region extraction; first layered network) and rotated by a rotation angle estimated from an orientation of a rectangle circumscribed around the mask image. Specifically, a part (a) and a part (b) of FIG. 8 illustrate rectangles that are circumscribed to the tablet region (region of pixel value 255) of the binarized mask image for a divided tablet (one-half the whole tablet) and a standing tablet (tablet with the cut surface in contact with a surface on which the tablet are placed), respectively. In this state, as illustrated in FIG. 9, the rectangular region can be divided into a plurality of regions (for example, two divisions in the horizontal direction and two divisions in the vertical direction, four divisions in total), and the percentage of white pixels (pixels with a pixel value of 255) in each region is calculated so that the determination described above can be made based on the distribution of the pixel values. Specifically, in the case of the divided tablet (half-tablet), it is asymmetrical on the +X and −X sides, and symmetrical on the +Y and −Y sides as illustrated in a part (a) of FIG. 9, and in the case of the standing tablet, it is almost symmetrical on the +X and −X sides, and on the +Y and −Y sides, as illustrated in a part (b) of FIG. 9. Therefore, the tablet determination part 100D can determine that the tablet is a divided tablet (half tablet) if it is asymmetric on the +X side and the −X side, and a standing tablet if it is symmetric (except for the one determined to be a whole tablet). In other words, it is determined that the tablet is divided when the external shape of the tablet (object) is of a predetermined shape (with the symmetry described above). Note that the neural network for region extraction described above can be configured by machine learning (GAN: Generative Adversarial Networks), such as a conditional GAN, which is given a separately created mask image as teacher data.

<Overview of Matching Processing>

Figure 10:
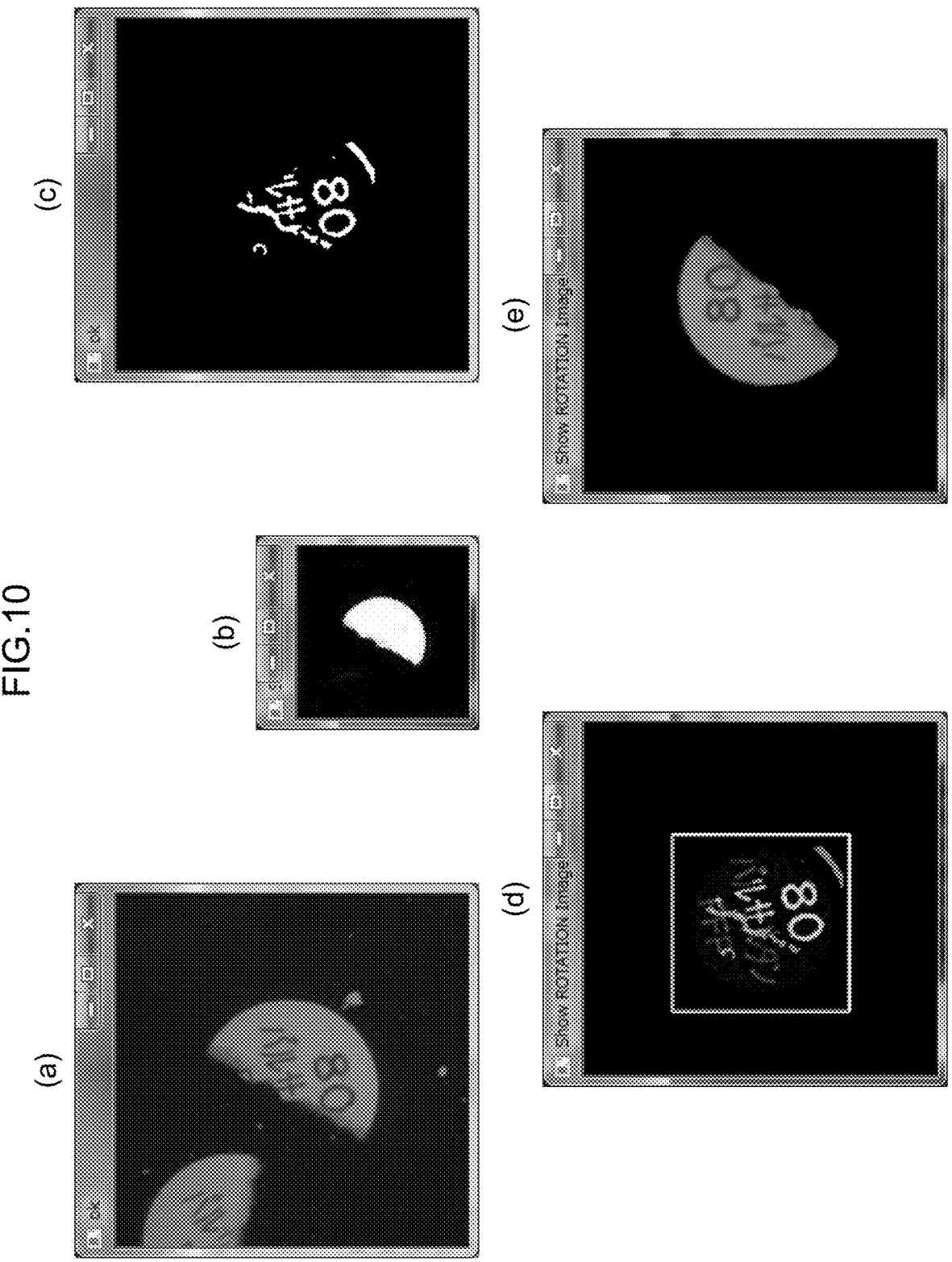
FIG. 10 is a drawing illustrating a situation where template matching is performed.

An overview of the matching processing (collation between the first image for matching with the second image for matching, which is the master image) in the tablet identification device 10 will be described. A part (a) of FIG. 10 is an example of a captured image containing a divided tablet, and the neural network for region extraction (first layered network) is used to generate a binarized mask image for such a captured image (a part (b) of the same figure). Then, the captured image and the binarized mask image are multiplied and preprocessed (for example, engraving extraction, binarization, inversion, etc.) to generate an image for matching (a part (c) of the same figure). Then, the matching score is calculated while relatively rotating the image for matching and the master image, and a rotation angle at which the score is maximized is determined (a part (d) of the same figure), and the image of the tablet region is rotated reversely by the rotation angle to align the orientation of printing or engraving with the master image (a part (e) of the same figure; the case of the second display processing). Such matching processing will be described in detail below.

<Generation of Image for Matching>

The image generation part 100E (first image acquisition part) generates an image for matching (first image for matching) for the divided tablet contained in the captured image (the first captured image) (step S140: image generating step, first image acquisition step). In order to identify the front surface and the back surface of the tablet, the image generation part 100E generates an image for matching for each of the images captured from the top and bottom with the cameras 210, 220 and maps these images. The generation of the image for matching will be described below.

Figure 11:
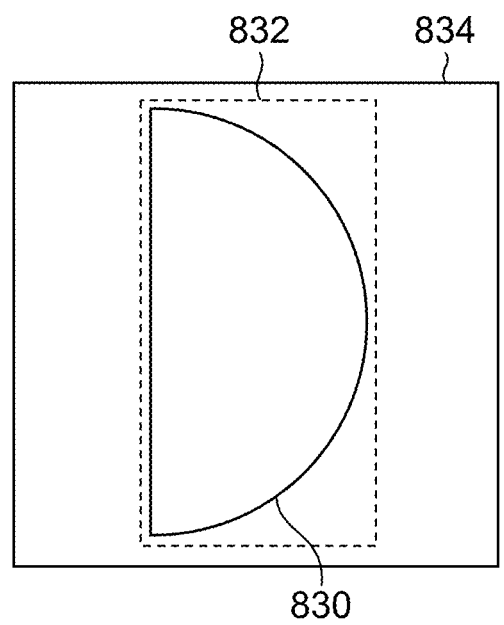
FIG. 11 is a drawing illustrating a half-tablet region being cut out.

The image generation part 100E generates an image for a mask using the neural network for region extraction (the first layered network), and preprocesses the generated mask image by binarization, shaping by closing, and the like. The neural network for region extraction can be the one used in determination of the divided tablet described above. Then, the image generation part 100E multiplies the preprocessed mask image and the captured image and performs extraction of the tablet region, removal of noise, etc. Further, the image generation part 100E finds a rectangle including the tablet region (for example, a rectangle that is circumscribed to the tablet region) and cuts out a range of a square including the rectangle from the captured image to prepare an image for matching. It is preferable to keep the rectangle upright after calculating the rotation angle. FIG. 11 illustrates an example of the relationship between the divided tablet region, rectangle, and images for matching (divided tablet region 830, rectangle 832, and image for matching 834) generated in this manner.

<Preprocessing for Image for Matching>

The preprocessing part 100I (collation part) performs preprocessing on the image for matching and/or the master image, the preprocessing including at least one of regional expansion processing, binarization processing, image inversion processing, printing and/or engraving region (part of the region including identification information) extraction processing, and printing and/or engraving emphasis processing (Step S150: Preprocessing Step and Collating Step). Note that it is preferable to align the image for matching with the master image to determine whether to perform the binarization processing, the image inversion processing, the printing and/or engraving region extraction processing, and the printing and/or engraving emphasis processing (emphasis on identification information). It is also desirable to align the size of the image for matching and the master image by enlarging or reducing the size of the image.

<Regional Expansion>

Figure 12:
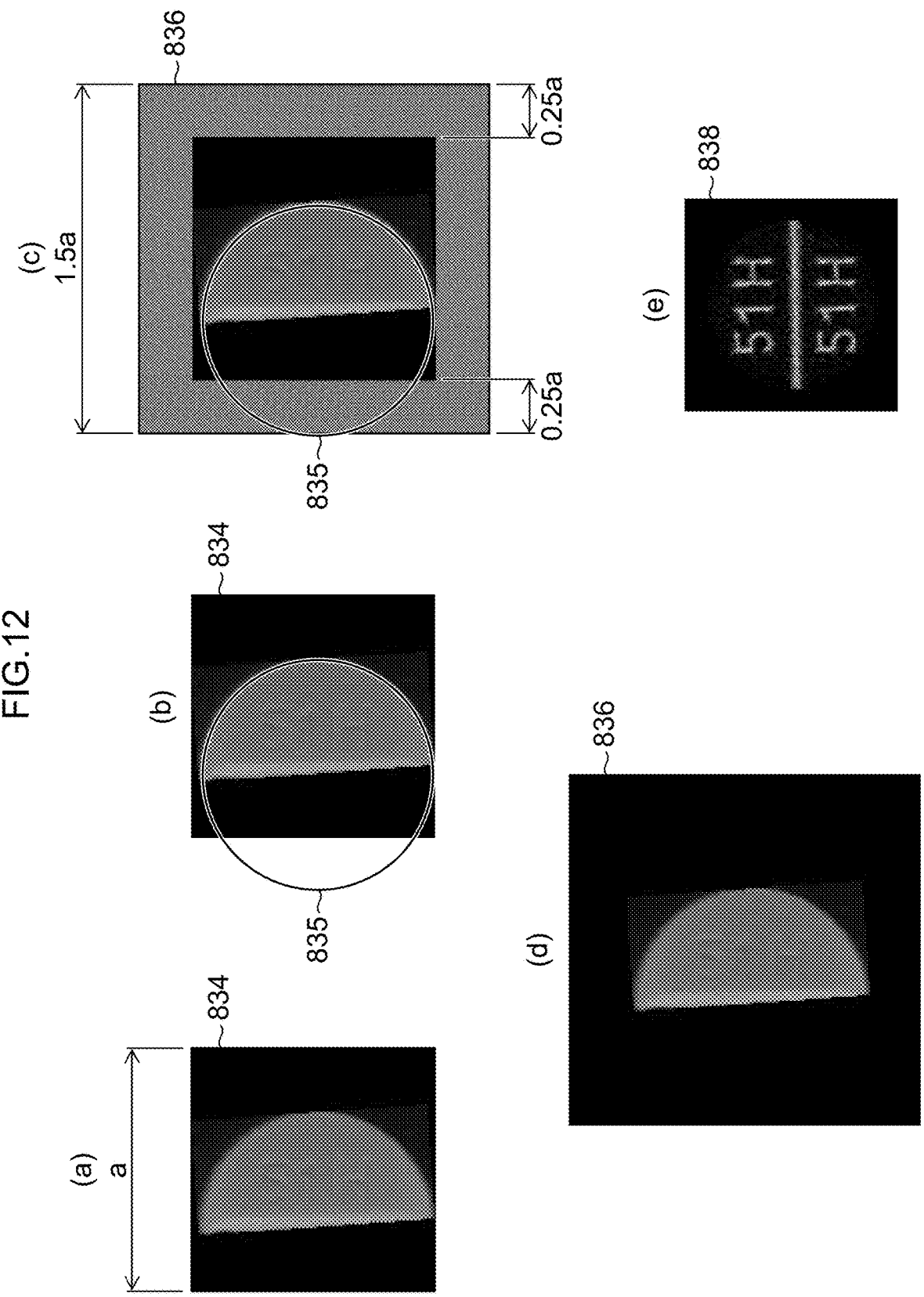
FIG. 12 is a drawing illustrating a situation where a region for template matching is expanded.

In the regional expansion as a preprocessing, the preprocessing part 100I expands the region so that the image for matching contains the circumscribed circle of the tablet region. For example, if the length of an edge of the image for matching 834 before expanding the region illustrated in a part (a) of FIG. 12 is "a", a part of the circumscribed circle 835 of the tablet region may protrude outside the image for matching 834, as illustrated in a part (b) of FIG. 12. Therefore, as illustrated in a part (c) of the same figure, if the region is enlarged by the increment of 0.25a on both sides and the length of the edges is set to "1.5a", the region can be enlarged to contain the circumscribed circle, and the image for matching 836 illustrated in a part (d) of FIG. 12 is obtained. A part (e) of FIG. 12 illustrates an example of a master image (master image 838) that has been preprocessed to extract the engraved portion.

The preprocessing part 100I may prepare an image for matching by cutting out a square range containing a range of the circumscribed circle 835 considering a margin area from the image for matching 836 and enlarging or reducing the size of the image to match the master image. This margin area can be on the order of (1/10)×a to (1/12)×a with respect to the circumscribed circle, for example ("a" is the length of one side of the square including the rotating rectangle described above). The margin area is secured by considering errors due to inclination and the like.

In addition to or instead of the regional expansion described above, the preprocessing part 100I may apply the binarization processing, the image inversion processing, and the engraving extraction processing to the image for matching. The engraving extraction can be performed by multiplication with the mask image generated using a neural network for engraving extraction (second layered network). The tablet identification part 100F performs template matching using the image for matching 836 after such preprocessing and the master image. The second layered network can be configured by performing machine learning by providing the image, from which the printing and/or engraving is extracted, as teacher data.

<Example of Tablet Region Image, Mask Image and Engraving Extraction Results>

Figure 13:
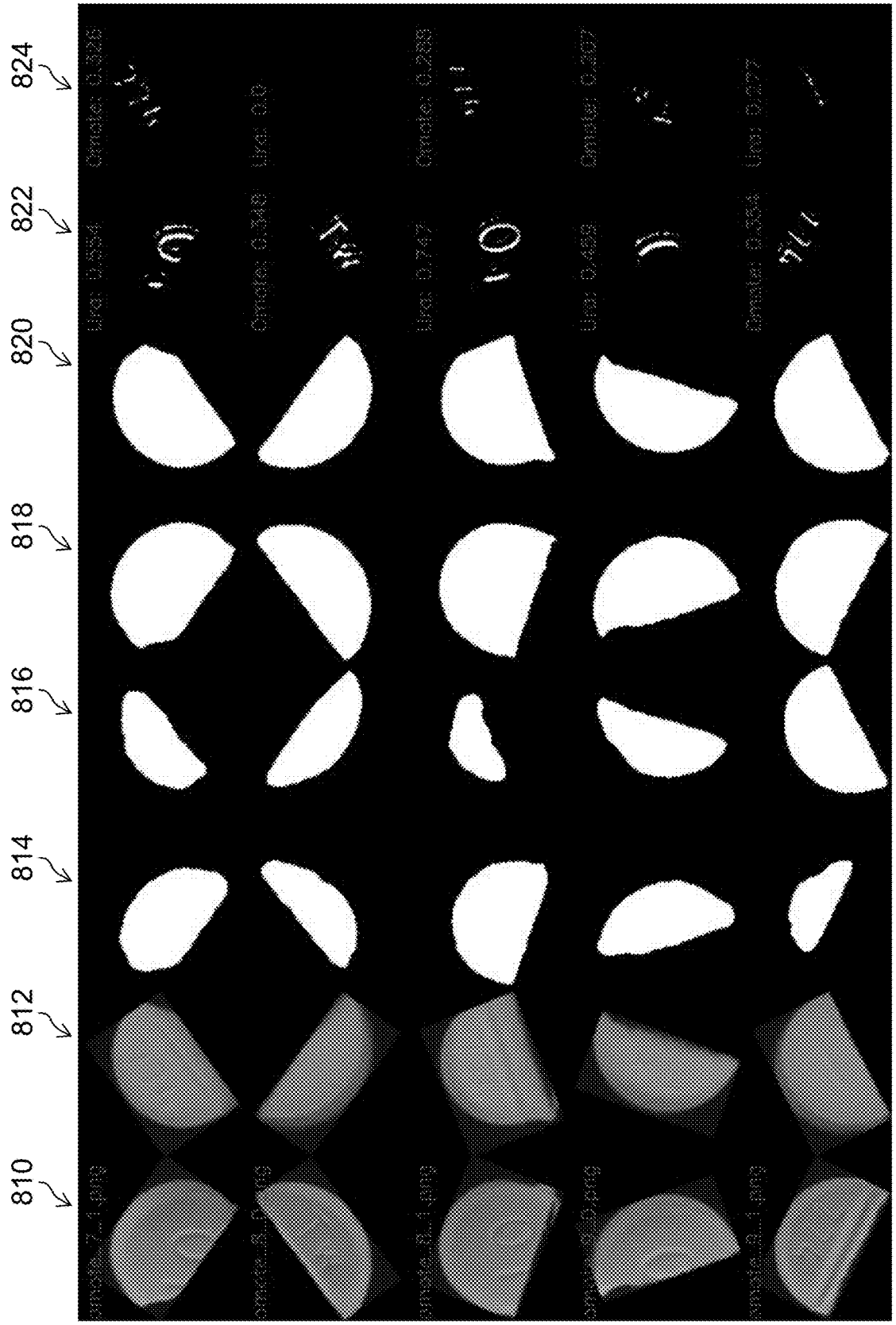
FIG. 13 is a drawing illustrating results of the extraction of drug region images, mask images, and engravings.

FIG. 13 illustrates an example of the extraction results of a tablet region image, a mask image for region extraction and engraving extraction, engraving, and the like. The column of reference numeral 810 indicates images (front or back of the tablets) of the rectangles (equivalent to rectangle 832 in FIG. 11) described above cut out from captured images, and the column of reference numeral 812 illustrates the opposite side of the images illustrated in the column of reference numeral 810 (back or front of the tablet). The columns of reference numerals 814, 816 illustrate the binarized mask images (front surface or back surface; equivalent to the images of reference numerals 810, 812) for engraving extraction, and the columns of reference numerals 818, 820 illustrate the binarized mask images (front surface or back surface; equivalent to the images of reference numerals 810, 812) for tablet region extraction. The mask images for engraving extraction are smaller than the mask image for tablet region extraction in order to eliminate the effects of reflection of side surfaces or surfaces of section caused by the inclination. The columns of reference numerals 822, 824 illustrate the result of extracting the engraving (front surface or back surface) from the images illustrated in the columns of reference numerals 810 and 812. In these images, the images in the same row are of the same tablet.

<Calculation of Matching Scores>

Figure 14:
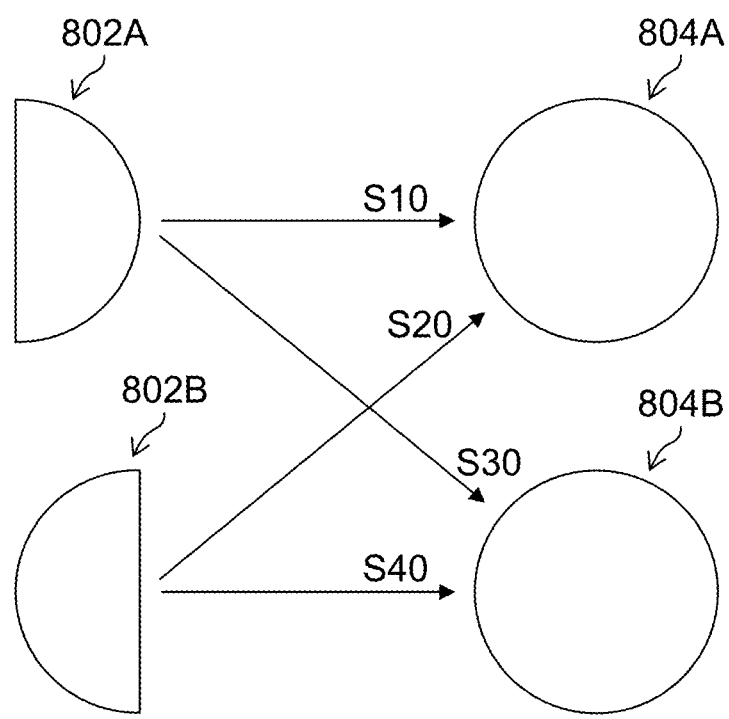
FIG. 14 is a drawing illustrating the calculation of the matching score being performed.

The tablet identification part 100F (collation part) calculates the matching score while rotating the image for matching (first image for matching) and the master image (second image for matching) relative to each other and repeats the calculation of the matching score while changing the rotation angle (Step S160: tablet identification step, collating step). FIG. 14 is a conceptual diagram illustrating the calculation of the matching score of the images for matching for the front surface and the back surface of the captured image and the master image for the front surface and the back surface of the tablet. Images 802A and 802B illustrate images of the divided tablets, one of which is the front surface and the other is the back surface. The master images 804A and 804B are the master images of the front surface and the back surface, respectively. In this situation, the tablet identification part 100F calculates matching scores S10 to S40 at each rotation angle. The matching scores S10 and S20 are matching scores for images 802A and 802B (images for matching) and master image 804A (front surface), respectively, and the matching scores S30 and S40 are matching scores for images 802A and 802B (images for matching) and master image 804B (back surface), respectively.

In calculating the matching score, (a) the matching score may be calculated while rotating these images relatively little by little with the centers of the image for matching and the master image aligned, or (b) a plurality of images with different rotation angles may be created and the matching scores may be calculated by moving each image. In addition, accurate matching can be achieved by reducing the change in rotation angle (for example, using 360 images with rotation angles that differ by 1 deg), but this may take long time for processing. In this case, rough matching may be performed by creating a small number of images with a large change in rotation angle (for example, using 36 images with rotation angles that differ by 10 deg), and then matching is performed near the angle with large scores as a result of the rough matching using images with a smaller change (using 10 images with rotation angles that differs by 1 deg) to speed up the processing.

<Calculation of Matching Score Considering Characteristics of Divided Tablets>

In normal template matching, it is common to use correlation score values (standardized). However, considering the characteristics of divided tablets, it is preferable to use a matching score (corrected score) as follows. Specifically, it is preferable that the tablet identification part 100F calculates (the correlation score value (standardized) in the template matching)×(the number of pixels of the image indicating the printing and/or engraving of the image for matching)×(the number of pixels of the image indicating the printed and/or engraved portion of the master image) as the matching score to identify the type and surface of the tablet based on the score. The reason why the "correlation score value (standardized)" is multiplied by the "number of pixels of the image indicating the printed and/or engraving of the image for matching" and the "number of pixels of the image indicating the printing and/or engraved portion of the master image" is to obtain scores increasing with an increase of the surface area of the printing and/or engraving and to increase the accuracy of the match by weighting complex printing and/or engraving even with the same "correlation score value (standardized)". In the calculation of such a corrected score, as the "number of pixels in the image indicating the printed and/or engraved portion", for example, the number of pixels of white pixels in images indicated in the column of reference numerals 822, 824 (images indicating the printing and/or engraved portion of the divided tablets) in FIG. 13 and the number of pixels of white pixels in a portion (e) in FIG. 12 (the image indicating the printing and/or engraved portion of the master image) may be used. The number of pixels of a parting line portion may be excluded when the "number of pixels of the image illustrating the printed and/or engraved portion" is obtained from the master image.

<Identification of Tablet Types>

Since divided tablets of a plurality of types are rarely packaged into one package bag, it is usually sufficient to perform matching for one type of master image. However, if a plurality of types of divided tablets are contained, the tablet identification part 100F compares the maximum values of the matching scores for the individual master images to specify that "the image for matching indicates the same tablet as the master image that has the largest matching score".

<Identification of Rotation Angle>

The tablet identification part 100F identifies the angle at which the matching score is maximized as the rotation angle of the tablet.

<Identification of Front Surface and Back Surface>

The tablet identification part 100F identifies the surface (front surface or back surface) of the tablet according to the following criteria, for example.

(1) If (maximum value of matching score S10)>(maximum value of matching score S30) and (maximum value of matching score S20)≤(maximum value of matching score S40), then image 802A represents the front surface and an image 802B represents the back surface.

(2) If (maximum value of matching score S20)>(maximum value of matching score S40) and (maximum value of matching score S10)≤(maximum value of matching score S30), then image 802A represents the back surface, and an image 802B represents the front surface.

The tablet identification part 100F determines whether or not the processing of all the divided tablets has been completed (Step S170) and repeats the processing from Step S140 to S160 until the determination is affirmed. If the determination of Step S170 is affirmed, the process for one package bag is completed and proceeds to step S180, and the processing of Steps S110 to S170 is repeated until the processing for all package bags is completed (until the determination of Step S180 is affirmed). If the determination in step S170 is affirmed, the process proceeds to Step S190.

<Display Processing>

Based on the results of identifying the type and the surface of the tablet, the display control part 100G displays a master image and an image for matching identified to show the same tablet and the same surface as the master image (an image for display that is determined to contain the same type of tablet (object) among the first images for matching) on a monitor 410 (display device) (step S190: display control step). In Step S190, a first display processing for displaying the tablets with chords, which is a straight-line portion of the divided tablet, aligned in orientation, or a second display processing for displaying the tablets with the printings and/or engravings of the divided tablets aligned in orientation is performed. The display control part 100G may perform any display processing in response to a user's instruction or may perform any of the display processing without a user's instruction. Note that, in the first and second display processing, the captured image and tablet region image may be displayed instead of the image for matching. When displaying an image for matching, an image without preprocessing may be used, or a preprocessed image may be used.

<First Display Processing>

Figure 24:
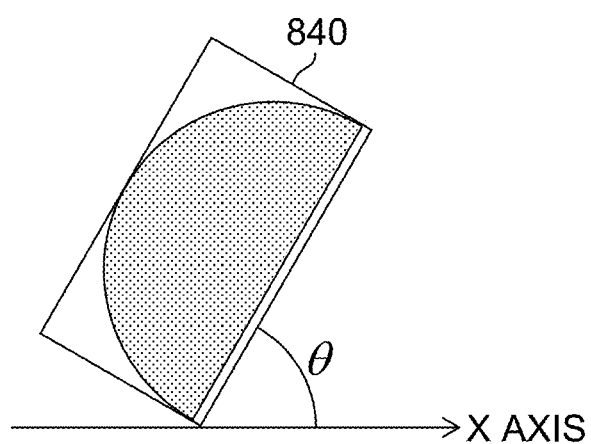
FIG. 24 is a drawing illustrating a rotation angle of a rectangle circumscribed to a divided tablet.

In the first display processing, the orientation of the chords in the image for matching (an example of the orientation of the outline of the object) is aligned for display. The chord of a tablet is an example of a divided line generated by dividing a tablet, which is an object, and if the tablet has a parting line, the divided line is generated near the parting line. The display control part 100G can determine, for example, a side with a small curvature, a short side, and a side near the center of the circumscribed circle as chords in the image for matching or the mask image. In calculating the orientation of the chord, the display control part 100G identifies the vertex coordinates of the rectangle 840 (circumscribed rectangle) circumscribed to the divided tablet (half tablet) and the rotation angle θ of the circumscribed rectangle from the X-axis (horizontal direction) as illustrated in FIG. 24. The display control part 100G then rotates the circumscribed rectangle (90 deg-θ deg) to make the circumscribed rectangle upright and obtains an image of the divided tablet upright (either the state of rectangle 841 or rectangle 842 in FIG. 25). The display control part 100G examines the pixel distribution of the upright divided tablets and identifies whether there are more bright pixels (pixels indicating the divided tablets; shaded area in FIG. 25) in the right half, as in rectangle 841, or there are many bright pixels in the left half, as in rectangle 842 (which can be identified based on the distribution of white pixels in the mask image, as described in method 2 of "Determination of Divided Tablets"). The orientation of the chords can be aligned in the horizontal direction by rotating clockwise by 90 deg for the state of rectangle 841 or counterclockwise by 90 deg for the state of rectangle 842. When displaying, the orientation of the chords may be aligned in the vertical direction or diagonally instead of the horizontal direction. When displaying a plurality of tablets, the orientation of the bows (the curved portion of the divided tablet) (an example of the orientation of the outline of the object) may be aligned in addition to the orientation of the chords of the respective tablets (see FIG. 16).

<Second Display Processing>

In the second display processing, the tablets are displayed with the printing and/or engraving (an example of identification information provided on the object) in the image for matching aligned in orientation. The display control part 100G can align the orientation of the printings and/or engravings by rotating the images for matching reversely by an angle corresponding to the rotation angle specified by the processing described above.

<Specific Examples of Display Processing>

The specific examples of the first and second display processing described above will be explained. The target tablet is "Valsartan Tablets 80 mg FFP", illustrated in FIG. 15. A part (a) of FIG. 15 is a front view (front surface) of the tablet, which has printing and a parting line. A part (b) of the same figure is a side view. The directional relationship between the parting line and the printing varies from tablet to tablet, and in some cases, the parting line is formed in the horizontal direction or in the vertical direction to the printing. Parts (c) and (d) of FIG. 15 illustrate rear views (back surface). The back surface also has printing as well as the front surface, but the orientation of printing is not consistent between the front surface and the back surface. For example, in contrast to the front surface illustrated in the part (a) of FIG. 15, the back surface may be like the part (c) (the orientation of the printing is the same as the front surface) or like the part (d) (the orientation of the printing is different from the front surface).

An example of the first display processing for the tablet described above is illustrated in FIG. 16. The part (a) of the same figure is a display of the front surface of the master image (the region on the left side of the white line) and the front surface of the image for matching (the region on the right side of the white line), while the part (b) of the same figure is a display of the back surface of the master image (the region on the left side of the white line) and the back surface of the image for matching (the region on the right side of the white line). In FIG. 16, the images present in the same positions in the parts (a) and (b) indicate the same tablet. An example of the second display processing is illustrated in FIG. 17. The part (a) of the same figure is a display of the front surface of the master image (the region on the left side of the white line) and the front surface of the image for matching (the region on the right side of the white line), while the part (b) of the same figure is a display of the back surface of the master image (the region on the left side of the white line) and the back surface of the image for matching (the region on the right side of the white line). In FIG. 17, the images present in the same position in part (a) and part (b) illustrate the same tablet. During the first and second display processing, the display control part 100G selects an image for matching (the first image for matching) for the front surface and/or the back surface of the tablet (object) and displays it on the monitor 410 (display device). It is also possible to display only the image of the front surface, or only the image of the back surface, or both images. Alternatively, the master image may be displayed at the same time or may be omitted from the display.

As explained above, according to the first embodiment, the divided tablets can be matched with desirable accuracy, and the first and second display processing can easily confirm the matching results.

<Matching in a Case where Oval Tablet is Divided>

Figure 18:
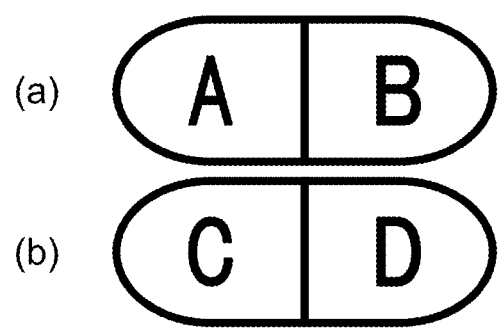
FIG. 18 is a drawing for explaining matching for an oval tablet.
Figure 19:
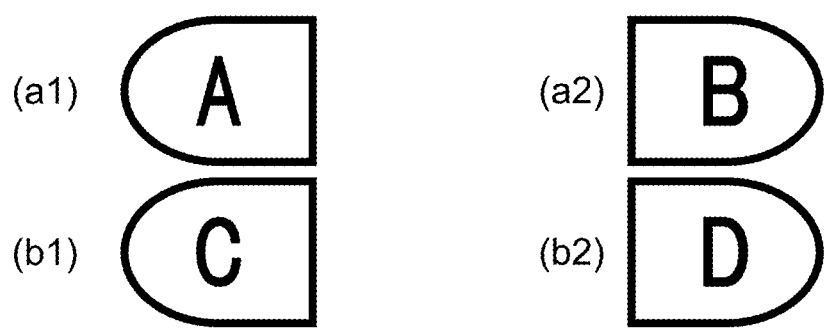
FIG. 19 is another drawing for explaining matching for an oval tablet.

The matching of a case where an oval-shaped tablet is divided. FIG. 18 is an example of a master image of an oval tablet, and a part (a) of the same figure illustrates the front surface of the tablet. The left and right sides of the front surface are engraved (or printed) with the letters "A" and "B" respectively. A part (b) of the same figure illustrates the back surface of the tablet. The letters "C" and "D" are engraved (or printed) on the left and right sides of the back surface, respectively. This tablet is provided with a parting line in the center. FIG. 19 illustrates a state in which the tablet in FIG. 18 is divided. Parts (a1) and (a2) in FIG. 19 illustrate the left side and the right side of the front surface, respectively, and parts (b1) and (b2) in the same figure illustrate the left and right sides of the back surface, respectively. In such oval-shaped tablets, some tablets have a different correspondence between the front surface and the back surface (the orientation of the engraving is different between the front surface and the back surface, as in the case of the valsartan tablets described above). For example, as illustrated in the parts (a1), (a2) of FIG. 20, the orientation of the engraving (up-down direction) may be the same on the front surface and the back surface, or the orientation of the engraving may be different as illustrated in parts (b1) and (b2) of the same figure.

<Calculating Matching Score for Oval Tablets>

Figure 21:
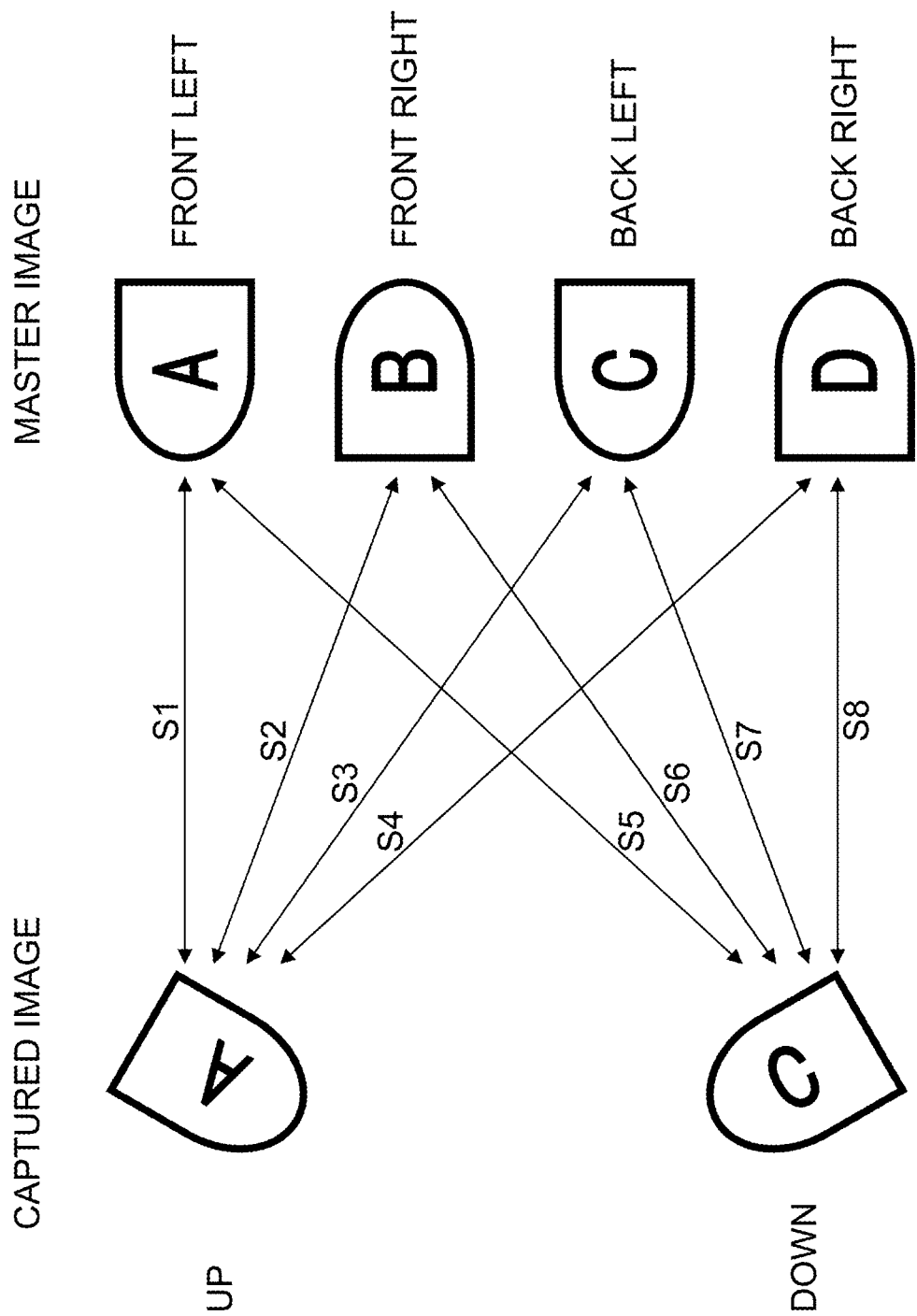
FIG. 21 is a drawing for explaining the calculation of matching score for an oval tablet.

FIG. 21 illustrates the matching of the oval tablets illustrated in FIGS. 18-20. In FIG. 21, an image marked with "up" is an image captured from above by camera 210, for example, and an image marked with "down" is an image captured from below by camera 220, for example. The captured images are engraved with one of A, B, C, or D, and the engraving on the captured images illustrated in FIG. 21 is an example. In this situation, the tablet identification part 100F calculates the following matching scores S1-S8 (equivalent to Step S160 of FIG. 7, tablet identification process). In this case, it is preferable to calculate a matching score that considers the characteristics of the divided tablet as well as the corrected score values described above. In the following explanation, "Matching score S1" may be referred to as "S1" (the same applies to matching scores S2-S8).

Matching score S1: Matching scores between the captured image (captured from above) and the master image (left side of the front surface)

Matching score S2: Matching scores between the captured image (captured from above) and the master image (right side of the front surface)

Matching score S3: Matching scores between the captured image (captured from above) and the master image (left side of the back surface)

Matching score S4: Matching scores between the captured image (captured from above) and the master image (right side of the back surface)

Matching score S5: Matching scores between the captured image (captured from below) and the master image (left side of the front surface)

Matching score S6: Matching scores between the captured image (captured from below) and the master image (right side of the front surface)

Matching score S7: Matching scores between the captured image (captured from below) and the master image (left side of the back surface)

Matching score S8: Matching scores between the captured image (captured from below) and the master image (right side of the back surface)

For example, the matching score S1 indicates the score value at the rotation angle that results in the maximum score among the template-matched score values obtained by rotating the master image (left side of the front surface) in a range of rotation angles from 0 deg to 359 deg with respect to the captured image (captured from above).

Correspondence between matching scores can be (S1, S7), (S1, S8), (S2, S7), (S2, S8), (S3, S5), (S3, S6), (S4, S5), and (S4, S6). Here, for example, (S1, S7) indicates "the image captured from above represents the left side of the front surface, and the image captured from below represents the left side of the back surface".

<Identification of Surface>

In the situation described above, the tablet identification part 100F identifies the surface of the oval-shaped divided tablet according to the following first and second methods. This allows matching of the oval-shaped divided tablets with desirable accuracy and the surfaces of the tablet can be identified. The type of tablet shall be separately specified (including cases where only one type of divided tablet is present in the prescription data or in the captured image of the package bag).

(First Method)

The tablet identification part 100F calculates the score T1=S1+S2+S7+S8, and the score T2=S3+S4+S5+S6 and compares the scores T1 and T2. As a result, if the score T1>T2, the tablet identification part 100F identifies "the image captured from above is the front surface and the image captured from below is the back surface". On the other hand, if the score T1<T2, the tablet identification part 100F identifies "the image captured from above is the back surface and the image captured from below is the front surface".

(Second Method)

The tablet identification part 100F calculates the score T1=S1+S7, score T2=S1+S8, score T2=S2+S7, score T4=S2+S8, score T5=S3+S5, score T6=S3+S6, score T7=S4+S5, score T8=S4+S6, and identifies the maximum score among the scores T1-T8. As a result, if the maximum score is one of the scores T1, T2, T7, or T8, the tablet identification part 100F identifies "the image captured from above is the front surface and the image captured from below is the back surface". On the other hand, if the maximum score is one of the scores T3, T4, T5, or T6, the tablet identification part 100F identifies "the image captured from above is the back surface and the image captured from below is the front surface".

<Display Processing>

In the case of the oval-shaped tablets described above, the display control part 100G also performs the first display processing for displaying the tablets with the chords, which are the straight-line portion of the divided tablets, aligned in orientation, or the second display processing for displaying the tablets with the printings and/or engravings of the divided tablets aligned in orientation, and displays the results on the monitor 410 (display device) as illustrated in FIGS. 16 and 17. This makes it easy to confirm the matching results.

<Case of Drug Differentiation>

Figure 22:
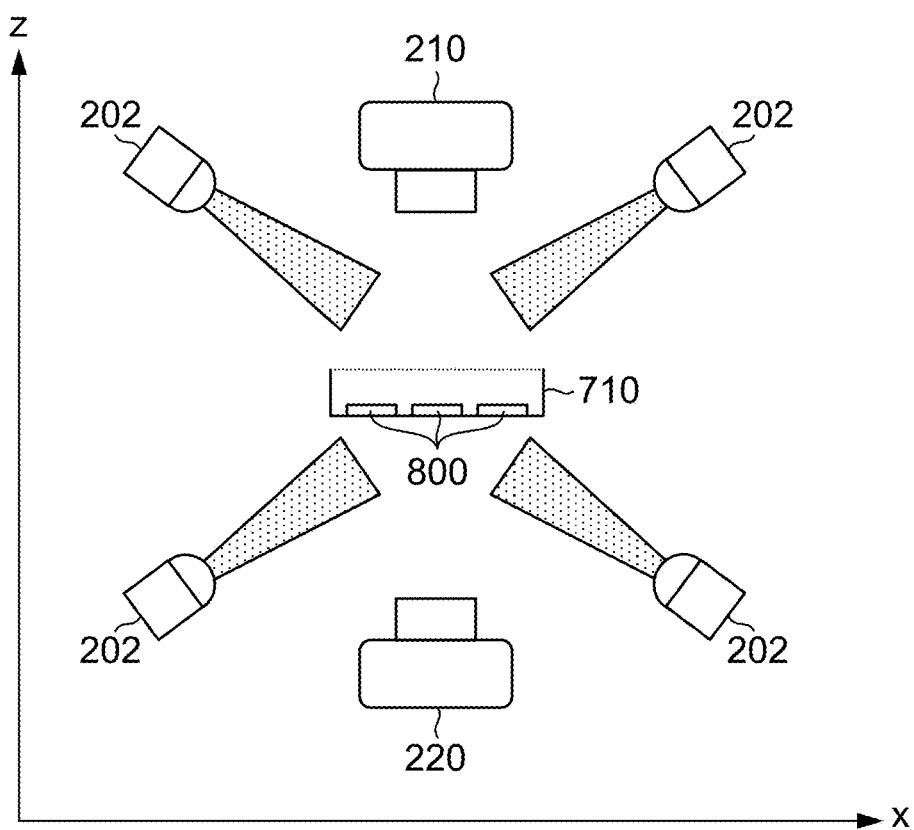
FIG. 22 is a side view illustrating the arrangement of light sources and cameras for drug differentiation.
Figure 23:
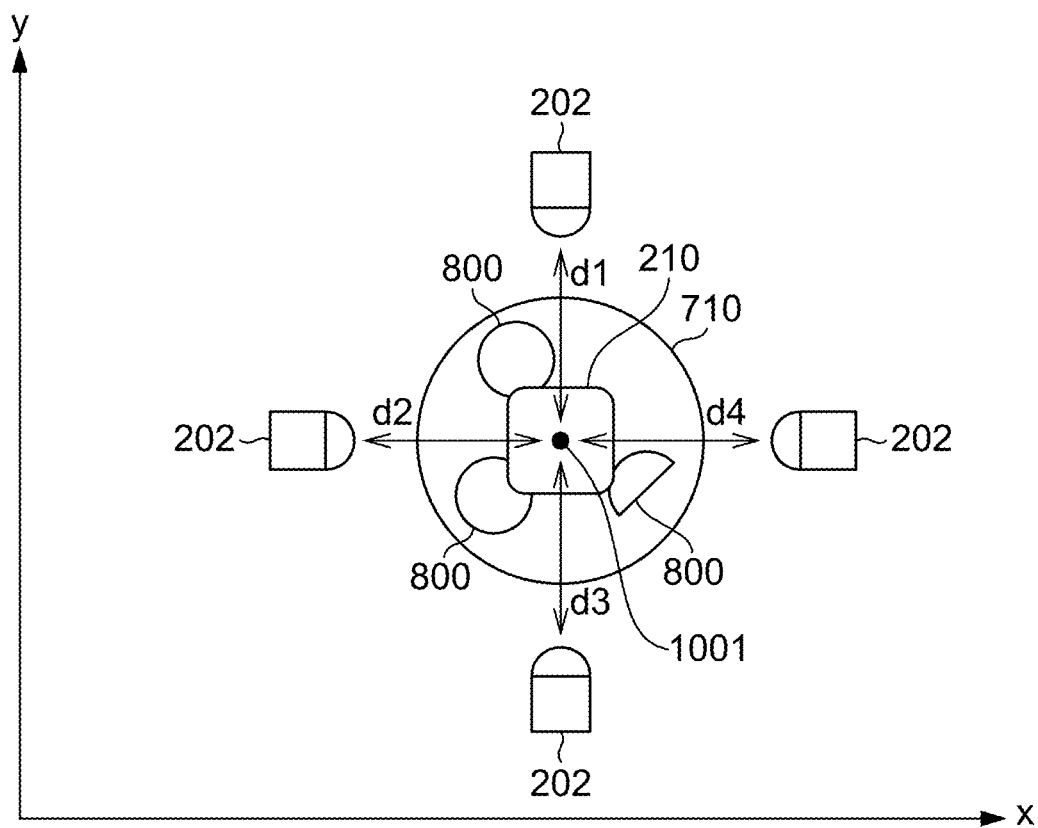
FIG. 23 is a plan view illustrating the arrangement of light sources and cameras for drug differentiation.

In the embodiments described above, identification of separately packaged drugs, which is mainly performed in support of a drug audit, has been described. However, the object collating device (tablet identification device) and the object collating method (tablet identification method) of the present invention can also be applied to the differentiation of drugs brought by a patient to a hospital, a pharmacy or the like. In the case of differentiation, as illustrated in the side view of FIG. 22, the tablets 800 is placed in a petri dish or other container 710 instead of a package bag to capture the image. FIG. 23 is a plan view of the state illustrated in FIG. 22. The other configurations for differentiation are the same as the tablet identification device 10 described above. The tablet identification processing can also be performed in the same manner as described above, but the prescription may not be confirmed when performing differentiation of the medicines brought to the hospital. In this case, the prescription data acquisition part 100A also enters characteristics of the drug (for example, type, shape, and color of the tablet, etc.) recognized visually or otherwise, or information such as the drug name, quantity, dosing method, and the like described in a notebook such as the so-called "medication handbook" as relevant information in response to the user's operation, and then uses such information instead of the prescription data.

Even in the case of drug differentiation, the object collating device (tablet identification device) and the object collating method (tablet identification method) of the present invention enables matching of divided tablets (objects which are dividable medical articles) with desirable accuracy, and the first and second display processing can easily confirm the matching results.

<Collation of Package Containing Tablets or Capsule-Type Drugs>

Although the example described above describes the case in which the collation is performed for tablets, the object collating device and the object collating method according to the present invention can be applied to a package containing tablets and a package containing capsule-type drugs. For example, so-called PTP packaging sheets (PTP: press through pack) are sheet-type package containing tablets or capsules in a state of being sandwiched between the plastic and aluminum foil and configured to allow the tablet and the like in-between to be taken out one by one by pressing a plastic portion formed three-dimensionally in conformity to the shape of the tablet or the capsule-type drug hard and breaking the aluminum foil. The PTP packaging sheet is also provided typically with a plurality of perforations and can be divided along these perforations. In other words, the PTP packaging sheet is another example of a dividable medical article.

Figure 26:
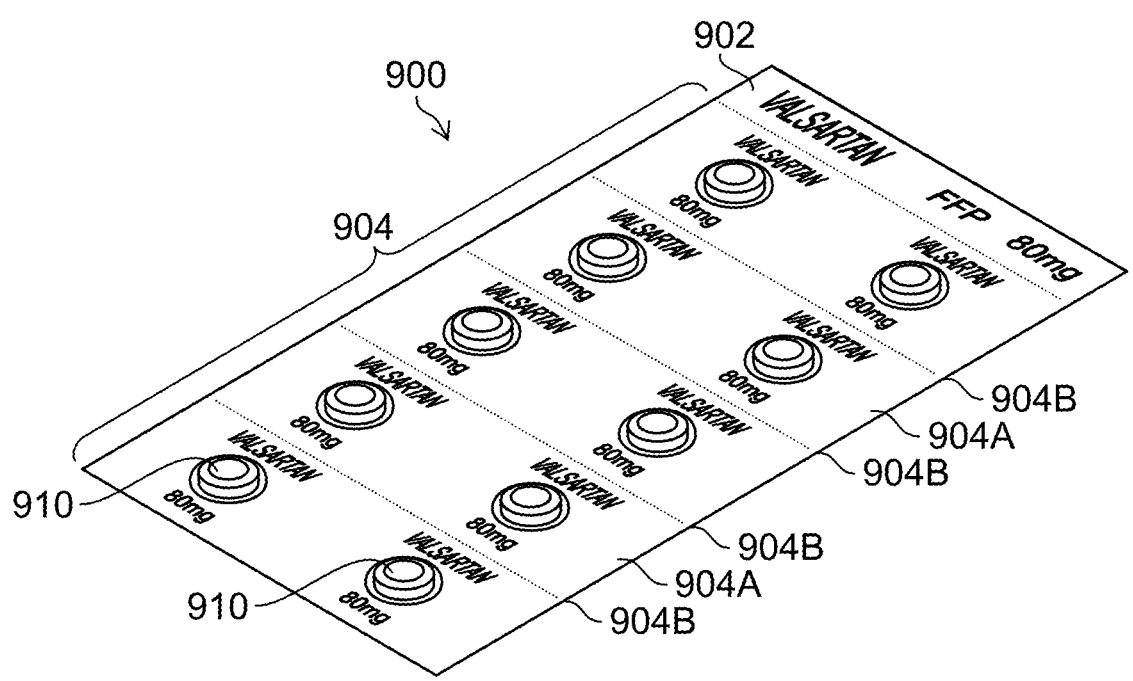
FIG. 26 is a perspective view illustrating an example of a sheet containing tablets (in an undivided state).
Figure 27:
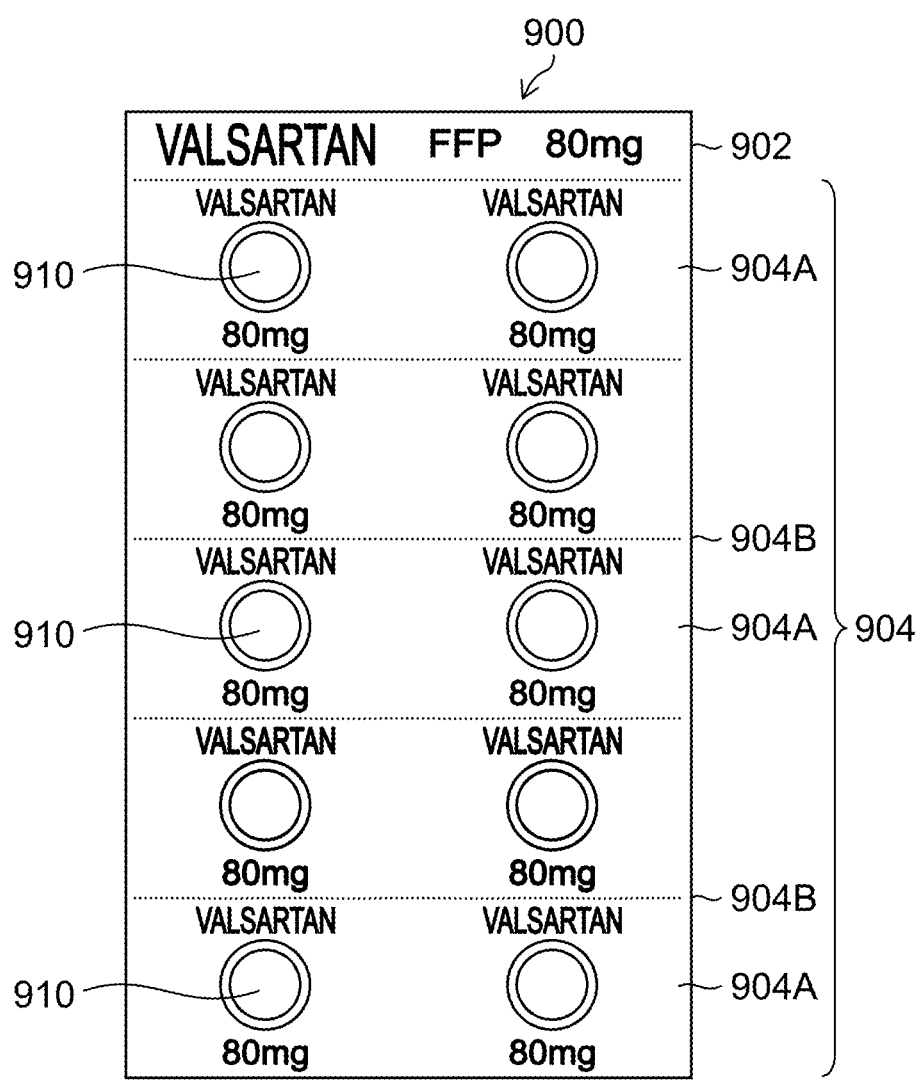
FIG. 27 is a front view illustrating an example of a sheet containing tablets (in an undivided state).
Figure 28:
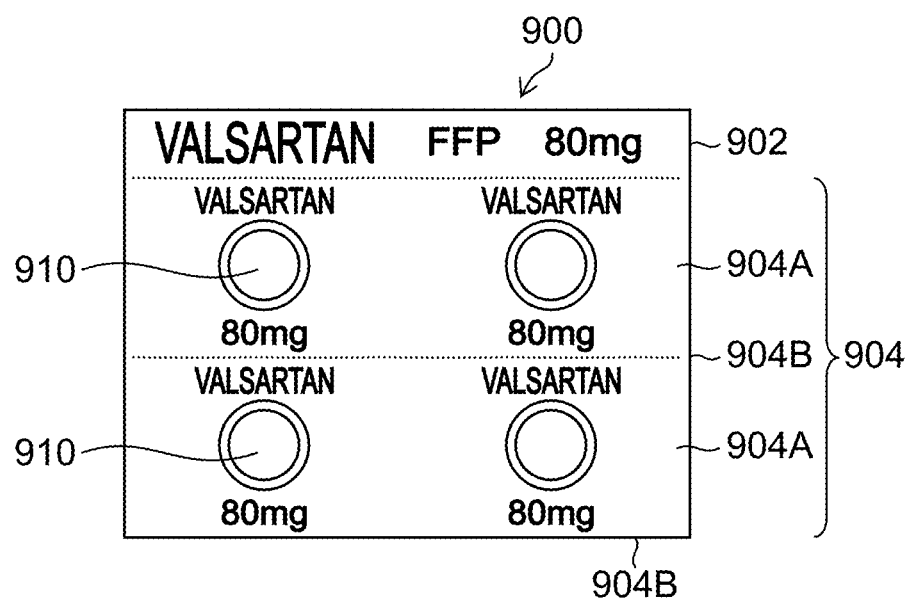
FIG. 28 is a drawing illustrating an example of a sheet containing tablets (in a divided state).

FIG. 26 is a perspective view of the PTP packaging sheet, a sheet 900 (undivided state), containing the tablets, viewed from the front surface side, and FIG. 27 is a front view. The name of the drug, the amount of the active ingredient, and other information on the sheet 900 is printed in letters and numbers on an end portion 902 and a main body 904 (an example of identification information; the same information is printed on the back surface), and by cutting (dividing) the main body 904 along the perforations 904B, the number of tablet portions 904A can be adjusted and the required number of tablets 910 can be obtained. The identification information in FIGS. 26 and 27 is described for convenience of explanation and does not accurately represent the actual product indication. FIG. 28 is a drawing illustrating an example of the sheet 900 with a portion of the main body 904 cut off. This is the case when it is divided up and provided to the patient according to the prescription, or when the part of the tablet taken out is cut out.

<Collation of Package of Tablets>

Such a sheet 900 can be collated in the same manner as for the tablets described above. Specifically, a master image (second image for matching based on the second captured image) is acquired by the camera 210, the camera 220, the image acquisition part 100B, and the master image acquisition part 100C for the front surface and the back surface of the sheet 900 (object) in an undivided state as illustrated in FIGS. 26 and 27, and a first image for matching based on the first captured image is acquired for the front surface and the back surface of the object of collation, the sheet 900 (in the undivided state, or in the divided state). The processing thereafter can be performed according to a flowchart illustrated in FIG. 7 as in the case of the tablet.

<Indication Example for Package>

Figure 29:
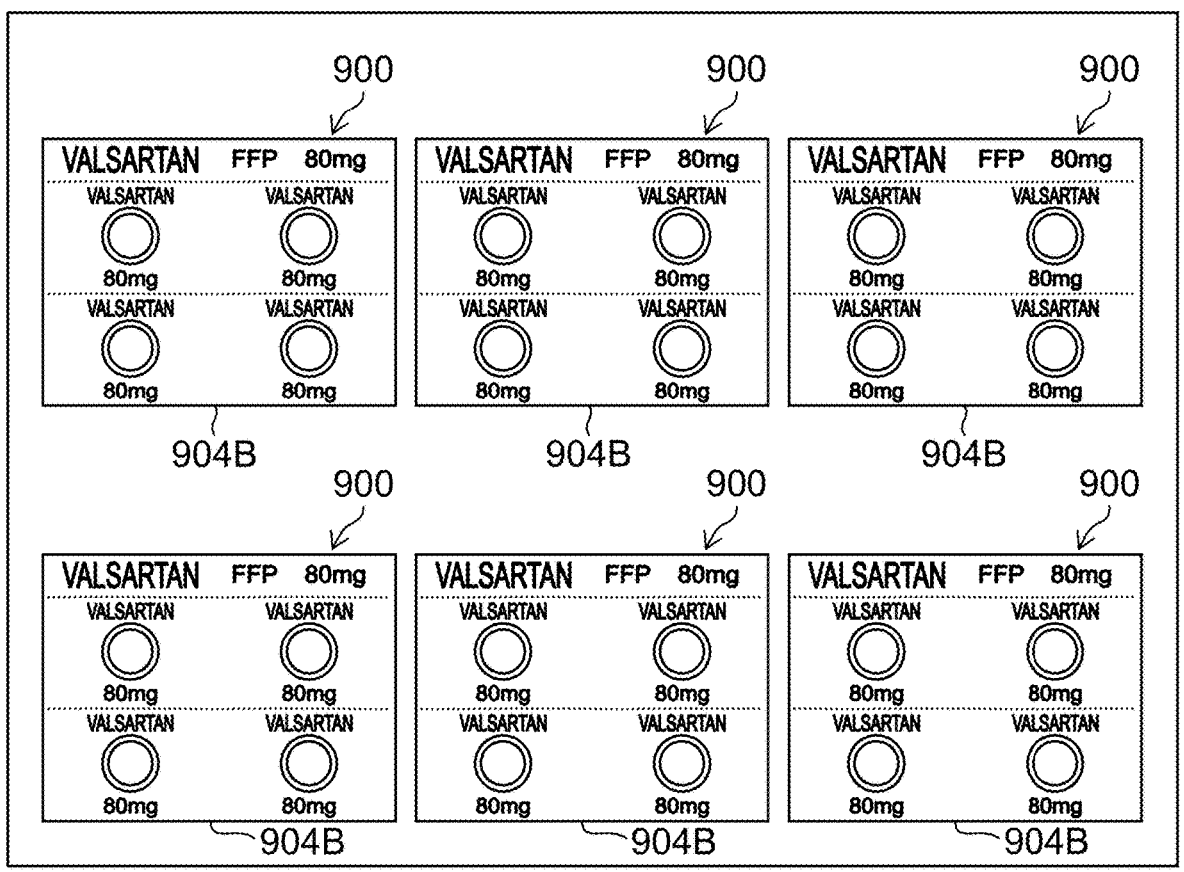
FIG. 29 is a drawing illustrating an example of the first display processing.
Figure 30:
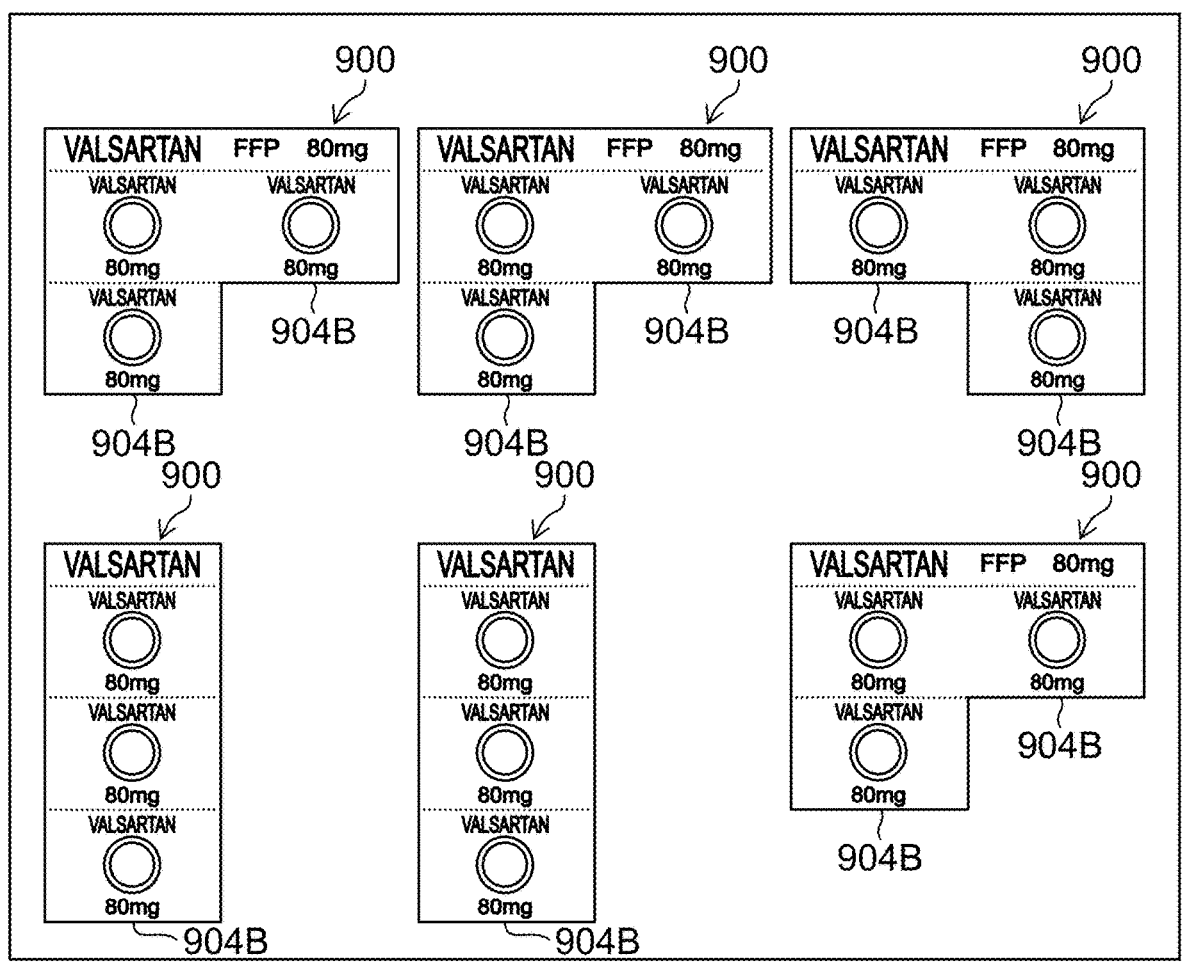
FIG. 30 is a drawing illustrating an example of the second display processing.

FIG. 29 illustrates an example of the first display processing for the divided sheet 900. In this example, the orientation of the outer shape of the sheet 900 is aligned by aligning the orientation of the perforations 904B, which are divided lines (and the orientation of the object with respect to the divided line). FIG. 29 is an example of a display for the front surface, but the back surface can be displayed in the same manner (see the example in FIG. 16). On the other hand, FIG. 30 illustrates an example of the second display processing for the divided sheet 900. The sheet 900 is not necessarily separated at the perforations 904B but may be separated in an orientation perpendicular to the perforations 904B by scissors or the like, in which case the shape of the sheet 900 after having divided may not be the same even if the number of tablets is the same. In such a case, a second display processing for displaying the tablets with the identification information (in this case, printing the name of the drug and the like) provided on the sheet 900 aligned in orientation can be performed. FIG. 30 is an example of display for the front surface, but the back surface can be displayed in the same way (see the example in FIG. 17).

The case of a package (PTP sheet) containing tablets has been described referring to FIGS. 26-30. However, also in the case of a sheet in which a capsule-type drugs are stored, the results can be displayed by the first and second display processing through collating in the same manner. The same collation and display processing can be performed in the same manner for a package of a type formed continuously into a sheet-shape with the bag-shaped compartments for containing the tablets individually.

In the case of a package containing tablets and a package containing a capsule-type drugs, it is possible to match the package with desirable accuracy as in the case of the tablets, and the matching results can be easily confirmed by the first and second display processing.

(Supplementary Note)

In addition to each aspect of the embodiments described above, the configurations described below are also included within the scope of the present invention.

(Supplementary Note 1)

The tablet identification device according to supplementary note 1 includes: an image acquisition part configured to acquire captured images obtained by capturing a tablet from a plurality of different directions: a master image acquisition part configured to acquire master images for a front surface and a back surface of an undivided tablet; a tablet determination part configured to determine whether or not the tablet contained in the captured image is a divided tablet, which is divided; an image generation part configured to generate an image for matching including a tablet region from a captured image of a tablet, which is determined to be a divided tablet; a tablet identification part configured to identify a type and a surface of the tablet included in the image for matching by template matching between the image for matching and the master image; and based on the results of identifying, a display control part configured to cause a display device to display a master image and an image for matching identified to show the same tablet and the same surface as the master image, and configured to perform a first display processing for displaying the tablets with chords, which are straight-line portions of the divided tablets, aligned in orientation, or a second display processing for displaying the tablets with printings and/or engravings of the divided tablets aligned in orientation.

In the configuration of Supplementary Note 1, since matching results of the divided tablets are displayed by the first display processing for displaying the tablets with chords, which are straight-line portions of the divided tablets, aligned in orientation or a second display processing for displaying the tablets with the printings and/or engravings of the divided tablets aligned in orientation, the user can easily figure out the result of identification (matching results) of the type and the surface of the tablet by eyesight. In the configuration of Supplementary Note 1, since template matching is performed using the master image of the undivided tablet, and thus the possibility of erroneous matching due to the match between small parts of the images can be reduced, and accurate matching can be performed. In this manner, according to the configuration of Supplementary Note 1, the divided tablets can be matched with desirable accuracy and the matching results can be easily confirmed.

In the configuration of Supplementary Note 1, it is preferable that the image acquisition part acquires images captured from a plurality of opposing directions. It is more preferable to acquire captured images of a front surface and a back surface of the tablet, such as perpendicularly from the top and bottom. The master image may be acquired based on the prescription data (information on the drug described in the prescription and information entered by the physician, pharmacist, and the like based on that information). The "identification" of tablets may be done through auditing of drugs, differentiation of medications brought to a hospital, and the like.

(Supplementary Note 2)

In the tablet identification device according to Supplementary Note 2, in the configuration of Supplementary Note 1, the display control part causes master images and images for matching to be displayed for the front surface and the back surface of the tablet. According to the configuration of Supplementary Note 2, the result of identification (matching result) can be figured out more easily. In the configuration of Supplementary Note 2, it is preferable to display the result of identification for each front surface and each back surface of the master image and the image for matching all at once.

(Supplementary Note 3)

The tablet identification device according to Supplementary Note 3, in the configuration of Supplementary Note 1 or Supplementary Note 2, further includes a whole tablet identification part that identifies the type of an undivided tablet based on the captured image and the master image, and the tablet determination part determines the tablet whose type has not been identified by the whole tablet identification part. According to the configuration of the supplementary note 3, processing can be efficiently performed by determining whether or not the tablet whose type is not identified by the whole tablet identification part is a divided tablet.

(Supplementary Note 4)

In the tablet identification device according to Supplementary Note 4, in any one of the configurations of Supplementary Note 1 to Supplementary Note 3, the tablet determination part generates a mask image including a tablet region from the captured image, and makes a determination based on a distribution of pixel values in the mask image. Undivided tablets are generally symmetrical in shape, such as circular, oval, and the like, but dividing creates asymmetrical orientations. For this reason, in the configuration of Supplementary Note 4, whether or not the tablet is a divided tablet is determined based on the distribution of pixel values (for example, asymmetry) in the mask image. An image including the tablet region with unnecessary portions such as noise is eliminated the captured image can be made into a mask image and may be binarized. The range of the mask image can be a rectangle that is circumscribed to the tablet region, for example, but is not limited to such an aspect. The tablet in a standing state (where a partitioning surface or a cut surface is in contact with the surface on which the tablet is placed; so-called "standing tablet") can also be determined based on the distribution of pixel values.

(Supplementary Note 5)

In the tablet identification device according to Supplementary Note 5, in the configuration of Supplementary Note 4, the tablet determination part generates a mask image using a first layered network constructed by machine learning. The first layered network can be a neural network, such as a CNN (Convolutional Neural Network), which is configured by performing machine learning, such as deep learning, and providing the mask image as teacher data.

(Supplementary Note 6)

In the tablet identification device according to Supplementary Note 6, in the configuration of Supplementary Note 5, the image generation part generates an image for matching by multiplying the pixel values of the captured image and the pixel values of the mask image pixel by pixel. The configuration of the supplementary note 6 specifies a specific aspect of processing for generating the image for matching generation processing, which can generate an image for matching with unnecessary portion removed by multiplication with the mask image.

(Supplementary Note 7)

The tablet identification device according to Supplementary Note 7, in any one of the configurations of Supplementary Note 1 to Supplementary Note 6, further includes a preprocessing part configured to perform preprocessing on the image for matching and/or the master image, the preprocessing including at least one of: regional expansion processing, binarization processing, image inversion processing, printing and/or engraving region extraction processing, and printing and/or engraving emphasis processing, the tablet identification part performs template matching by using the preprocessed image for matching and/or the master image. In the configuration of Supplementary Note 7, the preprocessing described above allows for even more accurate matching. These preprocessing may determine the type and/or the degree of processing to be performed in accordance with the user's instructions or may be determined by the tablet identification device instead of the user's instructions. Note that it is preferable to align the image for matching with the master image to determine whether to perform the binarization processing, the image inversion processing, the printing and/or engraving region extraction processing, and the printing and/or engraving emphasis processing as the preprocessing.

(Supplementary Note 8)

In the tablet identification device according to Supplementary Note 8, in the configuration of Supplementary Note 7, the preprocessing part performs processing for extraction processing the printing and/or engraving by a second layered network constructed by machine learning. The second layered network can be a neural network, such as a CNN (Convolutional Neural Network), which is configured by performing machine learning, such as deep learning, and providing the image from which the printing and/or engraving is extracted as teacher data.

(Supplementary Note 9)

In the tablet identification device according to Supplementary Note 9, in any one of the configurations of Supplementary Note 1 to 8, the tablet identification part calculates a matching score while rotating the image for matching and the master image relative to each other and performs identification based on the matching score. In the configuration of Supplementary Note 9, a matching score can be calculated for the image for matching for each of the plurality of orientations and for the front surface and back surface of the master image, and the type and surface of the tablet can be identified based on the result. The image may be rotated with the center of the circumscribed circle of the tablet region in the image for matching and the center of the master image aligned, or matching may be performed while moving the image which is rotated in advance. The matching may also include a relative movement (parallel movement) of the images.

(Supplementary Note 10)

In the tablet identification device according to Supplementary Note 10, in the configuration of Supplementary Note 9, the display control part, in the second display processing, calculates an angle of rotation at which the matching score to a specified surface becomes maximum and rotate the image for matching inversely by the angle to align the orientation of the printing and/or engraving in the image for matching with the master image. The configuration of Supplementary Note 10 specifically specifies the processing for aligning the orientation of printing and/or engraving in the image for matching with the master image in the second display processing.

(Supplementary Note 11)

In the tablet identification device according to Supplementary Note 11, in the configuration of Supplementary Note 9 or 10, the tablet identification part calculates the matching score using the correlation score value of the image for matching and the master image, the number of pixels of the image indicating printing and/or engraving, and the number of pixels of the image indicating printing and/or engraving of the master image. The configuration of Supplementary Note 11 specifies the calculation of a score for accurate matching, considering the characteristics of the divided tablets.

(Supplementary Note 12)

The tablet identification method according to Supplementary Note 12 includes: an image acquisition step for acquiring captured images obtained by capturing a tablet from a plurality of different directions; a master image acquisition step for acquiring master images for a front surface and a back surface of an undivided tablet; a tablet determination step for determining whether or not the tablet contained in the captured image is a divided tablet, which is divided; an image generating step for generating an image for matching including a tablet region from a captured image of a tablet, which is determined to be a divided tablet; a tablet identification step for identifying a type and a surface of the tablet included in the image for matching by template matching between the image for matching and the master image; and based on the results of identifying, a display control step for causing a display device to display a master image and an image for matching identified to show the same tablet and the same surface as the master image, and performing a first display processing for displaying the tablets with chords, which are straight-line portions of the divided tablets, aligned in orientation, or a second display processing for displaying the tablet with printings and/or engravings of the divided tablets aligned in orientation.

According to the configuration of Supplementary Note 12, the divided tablets can be matched with desirable accuracy as in the configuration of Supplementary Note 1, and the matching result can be easily confirmed.

The tablet identification method according to Supplementary Note 12 further includes the same configuration as in Supplementary Notes 2 to 11 may be further included. Also, a program for making the tablet identification device and a computer execute the tablet identification method of these aspects or a non-temporary recording medium that records computer-readable codes of the program may also be mentioned as an aspect of the present invention.

Although the embodiments and other aspects of the present invention have been described thus far, the invention is not limited to the aspects described above, and various modifications may be made without departing the spirit of the invention.

REFERENCE SIGNS LIST 10 tablet identification device
100 processing unit
100A prescription data acquisition part
100B image acquisition part
100C master image acquisition part
100D tablet determination part
100E image generation part
100F tablet identification part
100G display control part
100H whole tablet identification part
100I preprocessing part
110 CPU
120 ROM
130 RAM
200 lighting unit
202 light source
210 camera
220 camera
230 prescription reader
240 transport mechanism
300 memory
300A prescription data
300B captured image
300C image for matching
300D mask image
300E master image
300F result of identification
400 display unit
410 monitor
500 operation unit
510 keyboard
520 mouse
700 medicine package band
702 package bag
710 container
800 tablet 802A image
802B image
804A master image
804B master image
830 divided tablets region
832 rectangle
834 image for matching
835 circumscribed circle
836 image for matching
838 master image
840 rectangle
841 rectangle
842 rectangle
900 sheet
902 end portion
904 main body
904A tablet portion
904B perforation
910 tablet
100I image-capturing optical axis
θ rotation angle
S1 matching score
S2 matching score
S3 matching score
S4 matching score
S5 matching score
S6 matching score
S7 matching score
S8 matching score
S10 matching score
S20 matching score
S30 matching score
S40 matching score
S100 to S190 respective steps of tablet identification method
T1 score
T2 score
T3 score
T4 score
T5 score
T6 score
T7 score
T8 score

What is claimed is:

1. An object collating device comprising a processor, wherein the processor executes:
acquiring a first image for matching based on a first captured image of an object, the object being a dividable medical article;
acquiring a second image for matching based on a second captured image of the object in an undivided state;
determining the object contained in the first captured image is divided when an outline of the object is a predetermined shape;
collating the first image for matching and the second image for matching when the object is determined to be divided; and
causing a display device to display an image for display determined to contain the object of the same type in the first image for matching based on the result of the collation, and performing a first display processing for displaying the objects with outlines thereof aligned in orientation or a second display processing for displaying the objects with identification information attached thereto aligned in orientation.

2. The object collating device according to claim 1, wherein the processor executes:
acquiring the first image for matching for a front surface and a back surface of the object,
acquiring the second image for matching for the front surface and the back surface of the object in the undivided state,
performing the collation for the front surface and the back surface of the object, and
selecting the first image for matching for at least one of the front surface and the back surface of the object and causing the display device to display the first image for matching.

3. The object collating device according to claim 1, wherein the processor aligns an orientation of the outlines of the objects by aligning divided lines generated by dividing the objects in orientation in the first display processing.

4. The object collating device according to claim 1, wherein the processor performs the collation based on the outline and/or the identification information of the object.

5. The object collating device according to claim 1, wherein the processor extracts part of a region including at least one of the object and the identification information in the first image for matching and performs the collation for the part of the region.

6. The object collating device according to claim 1, wherein the processor performs the collation using an image applied with processing for emphasizing the identification information as at least one of the first image for matching and the second image for matching.

7. The object collating device according to claim 1, wherein the medical article is any one of a tablet, a package containing a tablet, and a package containing a capsule-type drug.

8. The object collating device according to claim 1, wherein the identification information includes at least one of printing and engraving provided on the object.

9. An object collating method executed by a processor, wherein the processor executes the steps of:
a first image acquisition step for acquiring a first image for matching based on a first captured image of an object, the object being a dividable medical article;
a second image acquisition step for acquiring a second image for matching based on a second captured image of the object in an undivided state;
a division determination step for determining whether or not the object contained in the first captured image is divided;
a collating step for collating the first image for matching and the second image for matching when the object is determined to be divided; and
a display control step for causing a display device to display an image for display determined to contain the object of the same type in the first image for matching based on the result of the collation, and performing a first display processing for displaying the objects with outlines thereof aligned in orientation or a second display processing for displaying the objects with identification information attached thereto aligned in orientation.

* * * * *